US012797837B2

(12) United States Patent

Laroche

(10) Patent No.: US 12,797,837 B2
(45) Date of Patent: Nov. 17, 2026

(54) TRANSITION METAL COMPLEX HYDROFORMYLATION CATALYST PRECUROR COMPOSITIONS COMPRISING SUCH COMPOUNDS, AND HYDROFORMYLATION PROCESSES

(71) Applicant: Dow Technology Investments LLC, Midland, MI (US)

(72) Inventor: Christophe R. Laroche, Lake Jackson, TX (US)

(73) Assignee: DOW TECHNOLOGY INVESTMENTS LLC, Midland, MI (US)

(*) Notice: Subject to any disclaimer, the term of this patent is extended or adjusted under 35 U.S.C. 154(b) by 345 days.

(21) Appl. No.: 18/696,139

(22) PCT Filed: Nov. 2, 2022

(86) PCT No.: PCT/US2022/079125
§ 371 (c)(1),
(2) Date: Mar. 27, 2024

(87) PCT Pub. No.: WO2023/114578
PCT Pub. Date: Jun. 22, 2023

(65) Prior Publication Data

US 2024/0399349 A1 Dec. 5, 2024

Related U.S. Application Data

(60) Provisional application No. 63/265,513, filed on Dec. 16, 2021.

(51) Int. Cl.
*B01J 31/18* (2006.01)
*B01J 31/40* (2006.01)
*C07C 45/50* (2006.01)

(52) U.S. Cl.
CPC ......... *B01J 31/186* (2013.01); *B01J 31/4053* (2013.01); *C07C 45/50* (2013.01); *B01J 2231/321* (2013.01); *B01J 2540/10* (2013.01)

(58) Field of Classification Search
CPC .......................... B01J 31/186; B01J 31/4053; B01J 2231/321; B01J 31/185; C07C 45/50
See application file for complete search history.

(56) References Cited

U.S. PATENT DOCUMENTS

| | | | |
|---|---|---|---|
| 4,148,830 | A | 4/1979 | Pruett et al. |
| 4,247,486 | A | 1/1981 | Brewester et al. |
| 4,599,206 | A | 7/1986 | Billig et al. |
| 4,668,651 | A | 5/1987 | Billig et al. |
| 4,694,109 | A | 9/1987 | Devon et al. |

(Continued)

FOREIGN PATENT DOCUMENTS

| | | |
|---|---|---|
| WO | 1997007086 | 2/1997 |
| WO | 2010003073 | 1/2010 |

(Continued)

*Primary Examiner* — Christina A Johnson
*Assistant Examiner* — Mordecai M Leavitt

(57) ABSTRACT

The present disclosure relates generally to transition metal complex hydroformylation catalytic precursor compositions, to hydroformylation processes, and to processes for separating one or more heavies from a hydroformylation reaction product fluid in hydroformylation processes comprising a metal-monophosphite ligand complex catalyst.

14 Claims, 2 Drawing Sheets

(56) References Cited

U.S. PATENT DOCUMENTS

| | | | | |
|---|---|---|---|---|
| 4,737,588 | A | 4/1988 | Billig et al. | |
| 4,774,361 | A | 9/1988 | Maher et al. | |
| 5,102,505 | A | 4/1992 | Sorensen | |
| 5,110,990 | A | 5/1992 | Blessing et al. | |
| 5,112,893 | A | 5/1992 | Wang | |
| 5,288,918 | A | 2/1994 | Maher et al. | |
| 5,430,194 | A | 7/1995 | Barner et al. | |
| 5,681,473 | A | 10/1997 | Miller et al. | |
| 5,728,893 | A | 3/1998 | Becker et al. | |
| 5,741,942 | A | 4/1998 | Bryant et al. | |
| 5,741,944 | A | 4/1998 | Bryant et al. | |
| 5,932,772 | A | 8/1999 | Argyropoulos et al. | |
| 6,307,109 | B1 | 10/2001 | Kanel et al. | |
| 10,981,851 | B2 | 4/2021 | Brammer | |
| 2012/0190894 | A1 | 7/2012 | Wegman | |
| 2015/0336861 | A1* | 11/2015 | Geilen | C08K 5/12 560/76 |
| 2015/0336988 | A1 | 11/2015 | Dyballa et al. | |
| 2021/0039079 | A1* | 2/2021 | Kim | C07C 45/505 |

FOREIGN PATENT DOCUMENTS

| | | |
|---|---|---|
| WO | 2016089602 | 6/2016 |
| WO | 2020240194 | 12/2020 |

* cited by examiner

TRANSITION METAL COMPLEX HYDROFORMYLATION CATALYST PRECUROR COMPOSITIONS COMPRISING SUCH COMPOUNDS, AND HYDROFORMYLATION PROCESSES

FIELD

The present inventions relate generally to transition metal complex hydroformylation catalytic precursor compositions, to hydroformylation processes, and to processes for separating one or more heavies from a hydroformylation reaction product fluid in hydroformylation processes comprising a metal-monophosphite ligand complex catalyst.

INTRODUCTION

It is known that various products and side products may be produced by reacting one or more reactants in the presence of a metal-organophosphorus ligand complex catalyst. However, stabilization of the catalyst and organophosphorus ligand remains a primary concern. Obviously catalyst stability is a key issue in the employment of any catalyst. Loss of catalyst or catalytic activity due to undesirable reactions of the highly expensive metal catalysts can be detrimental to the production of the desired product. Moreover, production costs of the product obviously increase when productivity of the catalyst decreases.

For instance, in hydroformylation processes, a cause of organophosphorus ligand degradation and deactivation of metal-organophosphorus ligand complex catalysts is due in part to vaporizer conditions present during, for example, a vaporizer step often employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created. It has been found that when a organophosphorus promoted rhodium catalyst is placed under such vaporizer conditions, it will deactivate at an accelerated pace with time. It is further believed that this deactivation is likely caused by the formation of an inactive or less active rhodium species. Such is especially evident when the carbon monoxide partial pressure is very low or absent. It has also been observed that when the catalyst comprises rhodium, the rhodium becomes susceptible to precipitation under prolonged exposure to such vaporizer conditions. For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium.

These degradation processes also increase the formation of acidic species as discussed in U.S. Pat. Nos. 4,599,206 and 5,288,918. These acids tend to accelerate the ligand hydrolysis degradation as well as catalyze aldehyde condensation reactions leading to increased heavies formation.

Another requirement for the vaporizer is heavies removal. The aldehyde product forms condensation products (dimer, trimes, etc.) commonly referred to as heavies as described in U.S. Pat. Nos. 4,148,830 and 4,247,486. The concentration of these heavies builds up and, with lower molecular weight aldehydes, typically reaches a steady state where the amount of heavies volatized and removed via the vaporizer equals the rate of their formation. However, as the product aldehyde molecular weight increases, the volatility of the heavies drops dramatically and the vaporizer may no longer able to remove them at the rate of formation even under drastic conditions.

Once the level of heavies builds up to undesirable levels, alternative removal processes are typically used. One such method is to purge a portion of the catalyst solution and send the purged solution to a precious metal recovery (PMR) facility to recover the valuable rhodium metal. Unfortunately, any contained product and ligand are lost in this process; in addition, the rhodium in this process is not available for production and thus represents idle capital.

Ultrafiltration and membrane separation techniques have been employed to separate active catalysts from the product and will typically also remove some heavies. Such membrane separation can be achieved as set out in U.S. Pat. Nos. 5,430,194 and 5,681,473. However, as the heavies are high molecular weight (as is the catalyst), the separation is difficult when attempting to minimize rhodium and ligand losses.

Organomonophosphites are well known ligands for use in hydroformylation and provide very active catalysts in many cases, particularly with branched higher molecular weight olefins. However, they are also known to be unstable and tend to suffer from precious metal losses during long-term operation. The balance of electronic and steric parameters on the ligand design for reactivity must be considered.

Accordingly, a highly active hydroformylation catalyst and a successful method for preventing and/or lessening degradation of the organophosphorus ligand and deactivation of the catalyst as occurs under harsh separation conditions would be highly desirable. Vaporization processes are limited due to the temperature sensitivities of the catalyst. Both phase separation and ultrafiltration processes separately suffer from inevitable catalyst losses via the separation process as neither are 100% effective in retaining the catalyst and/or ligand. Minimizing these losses while maintaining acceptable heavies levels in the catalyst solution over long periods of operation is desired.

SUMMARY

The present disclosure relates generally to transition metal complex hydroformylation catalytic precursor compositions, to hydroformylation processes, and to processes for separating one or more heavies from a hydroformylation reaction product fluid in hydroformylation processes comprising a metal-monophosphite ligand complex catalyst. In general, it has been found that using two steps for catalyst-products separation gives better results. The use of a vaporizer or other separation step to remove some or most of the product from the catalyst which remains in catalyst-enriched fluid, followed by a phase separation process on at least a portion of the resulting catalyst-enriched fluid to remove mostly heavies, allows the vaporizer to be optimized for product removal with minimal damage to the catalyst; further, the phase separation process maintains the heavies concentration to manageable levels with minimal rhodium losses. These and other advantages are discussed further herein.

Embodiments of the present invention utilize compounds according to formula (I):

(I)

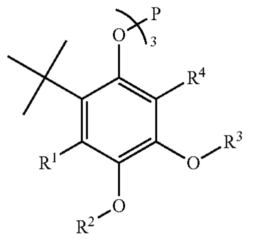

wherein $R^1$-$R^4$ are the same or different and each individually represent an hydrogen, a monovalent hydrocarbyl or substituted hydrocarbyl radical selected from alkyl, arylalkyl, and alicyclic radicals. In some embodiments, $R^1$ and $R^2$ may be linked to form cyclic moieties. In some embodiments, $R^2$ and $R^3$ may be linked to form cyclic moieties. In some embodiments, $R^3$ and $R^4$ may be linked to form cyclic moieties.

Such compounds can be used, for example, in transition metal complex hydroformylation catalyst precursor compositions. Thus, some embodiments of the present invention relate to transition metal complex hydroformylation catalytic precursor compositions. In one embodiment, a transition metal complex hydroformylation catalytic precursor composition consists essentially of a solubilized Group VIII transition metal-monophosphite complex, an organic solvent, and free monophosphite ligand, wherein the monophosphite ligand of the metal-monophosphite complex and the free monophosphite ligand are each a compound according to formula (I).

Some embodiments of the present invention relate to processes for separating one or more heavies from a hydroformylation reaction product fluid. In one embodiment, a process for separating one or more heavies from a hydroformylation reaction product fluid comprising a metal-monophosphite ligand complex catalyst, optionally free monophosphite ligand, one or more aldehyde products, and heavies, comprises:

(a) hydroformylating a $C_6$ to $C_{40}$ mono-olefin with the metal-monophosphite ligand complex catalyst and optionally free monophosphite ligand in a reaction zone to provide a hydroformylation reaction product fluid, wherein the monophosphite ligand comprises a compound according to formula (I)

(I)

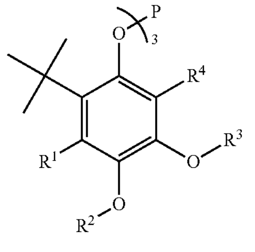

wherein $R^1$-$R^4$ are the same or different and each individually represent an hydrogen, a monovalent hydrocarbyl or substituted hydrocarbyl radical selected from alkyl, arylalkyl, and alicyclic radicals;

(b) removing a portion of the hydroformylation reaction product fluid from the reaction zone and transferring the portion to a product/catalyst separation zone wherein a portion of the aldehyde products are vaporized as an overhead stream and wherein a non-volatilized catalyst fluid comprising the metal-monophosphite ligand complex catalyst is recovered as a bottoms stream;

(c) mixing at least a portion of the bottoms stream obtained in step (b) in the presence of a nonpolar solvent and a polar solvent to obtain, by phase separation, two phases: a first phase comprising the polar solvent, the metal-monophosphite ligand complex catalyst and optionally free monophosphite ligand, and a second phase comprising the non-polar solvent, a portion of the heavies, and at least a portion of the remaining aldehyde products; and (d) recovering said metal-monophosphite ligand complex catalyst and at least a portion of any free monophosite ligand from the first phase and returning the recovered metal-monphosphite ligand complext catalyst and any recovered free monophosphite ligand to the reaction zone.

Some embodiments of the present invention relate to hydroformylation processes. In one embodiment, a hydroformylation process for producing aldehydes comprises reacting an olefinically unsaturated compound selected from the group consisting of alpha-olefins containing from 6 to 40 carbon atoms, internal olefins containing from 6 to 40 carbon atoms, and mixtures of such alpha and internal olefins with carbon monoxide and hydrogen in a reaction zone in the presence of a rhodium-monophosphite complex catalyst consisting essentially of rhodium complexed with carbon monoxide and at least one monophosphite ligand, wherein the at least one monophosphite ligand is a compound according to formula (I)

(I)

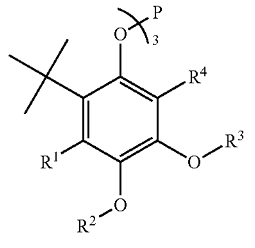

wherein $R^1$-$R^4$ are the same or different and each individually represent an hydrogen, a monovalent hydrocarbyl or substituted hydrocarbyl radical selected from alkyl, arylalkyl, and alicyclic radicals.

These and other embodiments are described further in the Detailed Description that follows.

DETAILED DESCRIPTION

Figure 1:
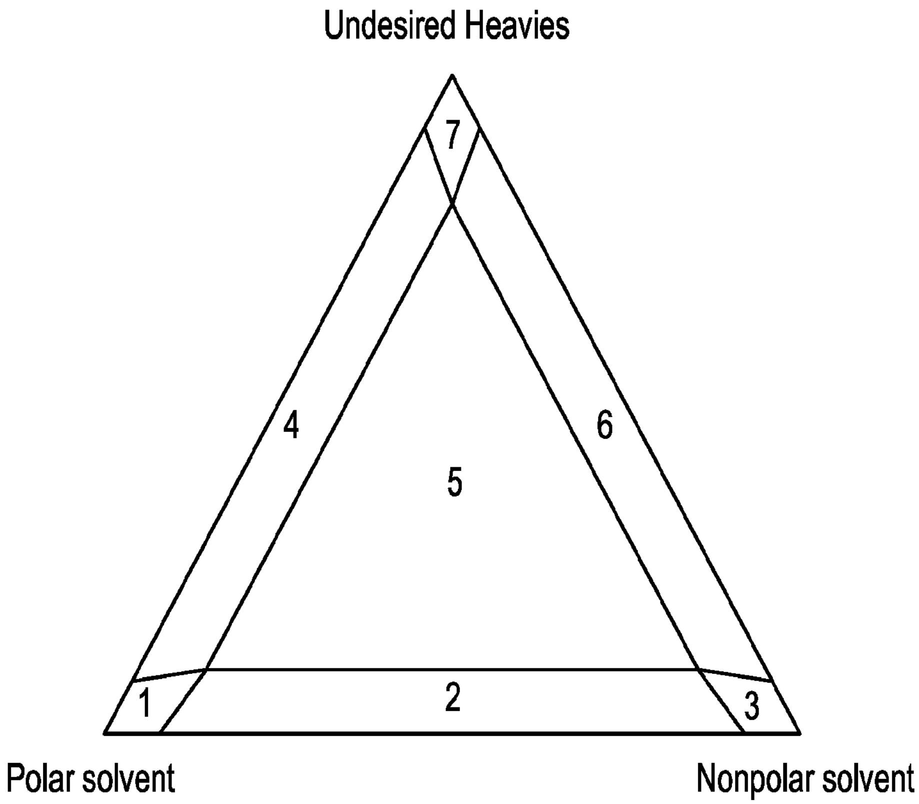
FIG. 1 is a ternary diagram identifying the phase behavior of total solvent systems used for the treatment of homogeneous catalyzed reaction effluents after a product/catalyst separation zone related to the removal of heavy by-products.

The disclosed process can be used, in some embodiments, in conjunction with a hydroformylation process that comprises contacting CO, $H_2$, and a $C_6$ to $C_{40}$ olefin under hydroformylation conditions sufficient to form at least one aldehyde product in the presence of a catalyst comprising, as components, rhodium and a monophosphite ligand according to formula (I). Optional process components include an amine and/or water.

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reaction zone, (b) a fluid stream on its way to a product/catalyst separation zone, (c) a fluid in a product/catalyst separation zone, (d) a recycle stream, (e) a fluid withdrawn from a reaction zone or product/catalyst separation zone, (f) a withdrawn fluid being treated with an acid removal system such as a filter or an extractor or other immiscible fluid contacting system, (g) a treated or untreated fluid returned to a reaction zone or product/catalyst separation zone, (h) a fluid in an external cooler, (i) a withdrawn fluid in a liquid-liquid separation zone (after the product/catalyst separation zone), (j) a separated fluid from a liquid-liquid separation zone (as in (i)) being returned to a reaction zone or product/catalyst separation zone, (k) a separated fluid from a liquid-liquid separation zone (as in (i)) comprising heavy by-products being removed from the system (optionally further processed). The liquid-liquid separation zone is a phase-separation zone wherein two liquid phases are present and are separated as discussed further herein.

"Hydrolyzable organophosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "free ligand" means ligand that is not complexed with (tied to or bound to) the metal, e.g., metal atom, of the complex catalyst.

As used herein, the terms "heavy byproducts" and "heavies" are used interchangeably and refer to byproducts that have a normal boiling point that is at least 25° C. above the normal boiling point of the desired product of the hydroformylation process. Such materials are known to form inherently in hydroformylation processes under normal operation through one or more side reactions, including for example, by aldol condensation.

As noted above, the present disclosure relates generally to transition metal complex hydroformylation catalytic precursor compositions, to hydroformylation processes, and to processes for separating one or more heavies from a hydroformylation reaction product fluid in hydroformylation processes comprising a metal-monophosphite ligand complex catalyst. In general, it has been found that using two steps for catalyst-products separation gives better results. The use of a vaporizer or other separation step to remove some or most of the product from the catalyst which remains in catalyst-enriched fluid, followed by a phase separation process on at least a portion of the resulting catalyst-enriched fluid to remove mostly heavies, allows the vaporizer to be optimized for product removal with minimal damage to the catalyst; further, the phase separation process maintains the heavies concentration to manageable levels with minimal rhodium losses.

For a commercially viable process, good reaction rates and catalyst stability must also be achieved. To achieve all of these goals in the hydroformylation of mono-olefins having 6 or more carbons ("C6+ mono-olefins"), specific monophosphite ligands, as described further herein, have been developed. The monophosphite ligands, in some embodiments, can advantageously balance a variety of factors to achieve good catalyst stability, hydrolysis resistance, and high reaction rate with the correct polarity to enable the required phase separation during the heavies removal but not come out of solution in the hydroformylation reaction system (particularly in a vaporizer tails stream, in embodiments where a vaporizer is used for the separation zone, where the catalyst concentration is highest and temperature the lowest).

In particular, in the context of hydroformylation of C6+ mono-olefins, a specific family of metal-organophosphorus ligand complex catalyzed processes have been discovered in which, according to some embodiments, heavies can be selectively extracted and separated from the catalyst-enriched fluid by phase separation. According to some embodiments, it is possible to separate the desired product from the reaction product fluid using vaporization and then remove the heavies without the need to use harsh vaporization separation and the harsh conditions associated therewith. Some embodimentso the present invention can thus provide a highly desirable separation method which prevents and/or lessens degradation of the organophosphorus ligand and deactivation of the catalyst which can occur under harsh conditions solely using vaporization separation.

This invention relates in part to a process for separating one or more products from a reaction product fluid as well as the heavies comprising metal-organomonophosphorus ligand complex catalysts comprising a specific family of organomonophosphorous ligands, optionally free organomonophosphorus ligand, optionally a nonpolar solvent, optionally a polar solvent, one or more heavies, and said one or more products, wherein said process comprises (1) vaporizing a product stream from the catalyst solution, (2) mixing a portion of the resulting catalyst and heavies-containing residue stream in the presence of a polar solvent and a nonpolar solvent, (3) separating the resulting mixture by phase separation to obtain a polar phase comprising said metal-organophosphorus ligand complex catalyst, optionally free organophosphorus ligand and said polar solvent and a non-polar phase comprising said one or more products, the heavies, and said non-polar solvent, and (4) recovering said polar phase from said nonpolar phase; wherein said organomonophosphorus ligand has a partition coefficient between the polar solvent and the nonpolar solvent of greater than about 2, and the heavies have a partition coefficient between the polar solvent and the nonpolar solvent of less than about 0.5.

Embodiments of the present invention utilize a compound according to formula (I):

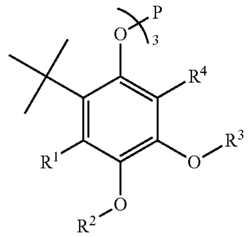

(I)

wherein $R^1$-$R^4$ are the same or different and each individually represent an hydrogen, a monovalent hydrocarbyl or substituted hydrocarbyl radical selected from alkyl, arylalkyl, and alicyclic radicals. In some embodiments, $R^1$ and $R^2$ may be linked to form cyclic moieties. In some embodiments, $R^2$ and $R^3$ may be linked to form cyclic moieties. In some embodiments, $R^3$ and $R^4$ may be linked to form cyclic moieties.

Such compounds can be used, for example, in transition metal complex hydroformylation catalyst precursor compositions according to some embodiments of the present invention. In one embodiment, a transition metal complex hydroformylation catalytic precursor composition consists essentially of a solubilized Group VIII transition metal-monophosphite complex, an organic solvent, and free monophosphite ligand, wherein the monophosphite ligand of the metal-monophosphite complex and the free monophosphite ligand are each a compound according to formula (I). By using the "consisting essentially of" transitional phrase, components that would materially change the characteristics of the transition metal complex hydroformylation catalyst precursor composition are excluded. Non-limiting examples of such components that would be excluded are other ligands that would interfere with partitioning of the rhodium (or other catalytic metal) in the reaction fluid into polar and nonpolar phases as described herein in connection with some embodiments of the present invention such as phosphines, polyorganophosphites, and monophosphites other than those according to formula (I). In some embodiments, the monophosphite ligand of the metal-monophosphite complex and the free monophosphite ligand are the same compound according to formula (I). In some embodiments, when the compound according to formula (I) is used as a ligand in a hydroformylation process, the ligand can facilitate a fast hydroformylation rate, thermal stability, and/or favorable partitioning into a polar organic solvent.

Some embodiments of the present invention relate to processes for separating one or more heavies from a hydroformylation reaction product fluid. In one embodiment, a process for separating one or more heavies from a hydroformylation reaction product fluid comprising a metal-monophosphite ligand complex catalyst, optionally free monophosphite ligand, one or more aldehyde products, and heavies, comprises:

(a) hydroformylating a $C_6$ to $C_{40}$ mono-olefin with the metal-monophosphite ligand complex catalyst and optionally free monophosphite ligand in a reaction zone to provide a hydroformylation reaction product fluid, wherein the monophosphite ligand comprises a compound according to formula (I);

(b) removing a portion of the hydroformylation reaction product fluid from the reaction zone and transferring the portion to a product/catalyst separation zone wherein a portion of the aldehyde products are vaporized as an overhead stream and wherein a non-volatilized catalyst fluid comprising the metal-monophosphite ligand complex catalyst is recovered as a bottoms stream;

(c) mixing at least a portion of the bottoms stream obtained in step (b) in the presence of a nonpolar solvent and a polar solvent to obtain, by phase separation, two phases: a first phase comprising the polar solvent, the metal-monophosphite ligand complex catalyst and optionally free monophosphite ligand, and a second phase comprising the non-polar solvent, a portion of the heavies, and at least a portion of the remaining aldehyde products; and (d) recovering said metal-monophosphite ligand complex catalyst and at least a portion of any free monophosite ligand from the first phase and returning the recovered metal-monphosphite ligand complext catalyst and any recovered free monophosphite ligand to the reaction zone.

In some embodiments, the recovered metal-monophosphite ligand complex catalyst and any recovered free monophosphite ligand from step (d) can be used in the reaction zone without further treatment. In some embodiments, the polar solvent present in step (d) is removed from the first phase prior to the recovered metal-monophosphite ligand complex catalyst and any recovered free monophosphite ligand being returned to the reaction zone. In some embodiments, the non-polar solvent is distilled from the second phase in step (d) and at least partially recycled. In some embodiments, the non-polar solvent comprises a $C_6$-$C_{40}$ mono-olefin and is the same as the mono-olefin being hydroformylated in step (a). In some embodiments, the non-polar solvent comprises unreacted mono-olefin that is recovered from the overhead stream in step (b).

Some embodiments of the present invention relate to hydroformylation processes. In one embodiment, a hydroformylation process for producing aldehydes comprises reacting an olefinically unsaturated compound selected from the group consisting of alpha-olefins containing from 6 to 40 carbon atoms, internal olefins containing from 6 to 40 carbon atoms, and mixtures of such alpha and internal olefins with carbon monoxide and hydrogen in a reaction zone in the presence of a rhodium-monophosphite complex catalyst consisting essentially of rhodium complexed with carbon monoxide and at least one monophosphite ligand, wherein the at least one monophosphite ligand is a compound according to formula (I). In some embodiments, the reaction zone further comprises at least one free monophosphite ligand, wherein the at least one free monophosphite ligand is a compound according to formula (I). In some embodiments, the hydroformylation reaction conditions comprise: a reaction temperature from 50° C. to 120° C., a total gas pressure of hydrogen, carbon monoxide, and olefinically unsaturated organic compound from 1 to 1500 psia, a hydrogen partial pressure from 15 to 200 psia, and a carbon monoxide partial pressure from 10 to 200 psia, and wherein the reaction zone contains from 4 to 100 moles of said monophosphite ligand per mole of rhodium. In some embodiments, the concentration of rhodium in the reaction zone is 5 to 500 ppmw. In some embodiments, the second phase comprising non-polar solvent and heavies isolated in step (c) is further processed to recover residual aldehyde product. In some embodiments, at least a portion of the nonpolar solvent and/or polar solvent used in step (c) is provided with the bottoms stream from step (b).

Turning now to starting materials used in hydroformylation, hydrogen and carbon monoxide may be obtained from any suitable source, including petroleum cracking and refinery operations.

Syngas (from synthesis gas) is the name given to a gas mixture that contains varying amounts of CO and $H_2$. Production methods are well known and include, for example: (1) steam reforming and partial oxidation of natural gas or liquid hydrocarbons, and (2) the gasification of coal and/or biomass. Hydrogen and CO typically are the main components of syngas, but syngas may contain carbon dioxide and inert gases such as $CH_4$, $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications. Syngas mixtures are preferred as a source of hydrogen and CO.

In some embodiments, the olefin starting material reactants comprise one or more $C_6$ to $C_{40}$ olefins. In some embodiments, the olefin starting material reactants that may be employed in the hydroformylation process of this invention include both optically active (prochiral and chiral) and non-optically active (achiral) olefinic unsaturated compounds containing from 6 to 40, preferably 8 to 20, carbon atoms. Such olefinic unsaturated compounds can be substituted or unsubstituted, terminally or internally unsaturated, straight-chain, branched chain or cyclic. Olefin mixtures, such as obtained from the oligomerization of ethylene, propene, butene, isobutene, etc. (such as so called dimeric, trimeric or tetrameric propylene and the like, as disclosed, for example, in U.S. Pat. Nos. 4,518,809 and 4,528,403) can be employed. Moreover, such olefin compounds may further contain one or more additional ethylenic unsaturated groups, and mixtures of two or more different olefinic unsaturated compounds may be employed as the starting hydroformylation material if desired. For example, commercial alpha olefins containing six or more carbon atoms may contain minor amounts of corresponding internal olefins and/or their corresponding saturated hydrocarbon and that such commercial olefins need not necessarily be purified from same prior to being hydroformylated. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809, 4,769,498 and the like.

Some embodiments of the present invention are especially useful for the production of non-optically active aldehydes, by hydroformylating achiral alpha-olefins containing from 6 to 40, preferably 8 to 20, carbon atoms, and achiral internal olefins containing from 6 to 20 carbon atoms as well as starting material mixtures of such alpha olefins and internal olefins.

Illustrative alpha and internal olefins that can be hydroformylated according to some embodiments of the present invention include, for example, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-octene, propylene dimers, propylene trimers, propylene tetramers, 2-ethyl-1-hexene, 1,4-hexadiene, 1,7-octadiene, 3-cyclohexyl-1-butene, and the like.

Prochiral and chiral olefins useful in the asymmetric hydroformylation that can be employed to produce enantiomeric aldehyde mixtures include those represented by the formula:

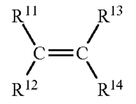

wherein $R^{11}$, $R^{12}$, $R^{13}$ and $R^{14}$ are the same or different (provided $R^{11}$ is different from $R^{12}$ or $R^{13}$ is different from $R^{14}$) and are selected from hydrogen; alkyl; substituted alkyl. The prochiral and chiral olefins of this definition also include molecules of the above general formula where the R groups are connected to form ring compounds, e.g., 3-methyl-1-cyclohexene, and the like.

As indicated above, the processes of this invention are conducted in the presence of one or more nonpolar solvents and one or more polar solvents, or in the presence of one or more nonpolar solvents followed by mixing with one or more polar solvents, or in the presence of one or more polar solvents followed by mixing with one or more nonpolar solvents. Depending on the particular catalyst and reactants employed, suitable nonpolar reaction and extraction solvents include, for example, alkanes, cycloalkanes, alkenes, alkadienes, aldehydes, ketones, ethers, esters, amines, aromatics, silanes, silicones, carbon dioxide, and the like. Examples of unsuitable nonpolar solvents include fluorocarbons and fluorinated hydrocarbons. These are undesirable due to their high cost, risk of environmental pollution, and the potential of forming multiphases. In some embodiments, the one or more reactants, metal-organophosphorus ligand complex catalyst, and optionally free organophosphorus ligand exhibit sufficient solubility in the nonpolar solvent or polar solvent such that phase transfer agents or surfactants are not required.

Mixtures of one or more different nonpolar solvents may be employed if desired. The amount of polar and/or nonpolar solvent employed in the extraction and separation zone, if any, is not critical to the subject invention and need only be that amount sufficient to provide the reaction medium with the particular metal concentration desired for a given process. The amount of non-polar solvent employed in the reaction zone is not critical to the subject invention and need only be that amount sufficient to extract one or more heavy by-products from the reaction product fluid in the liquid-liquid separation zone for any given process and not result in catalyst component precipitation. To illustrate considerations in determining the amount of nonpolar solvent to employ, reference will now made to FIG. 1, which is a ternary diagram identifing the phase behavior of total solvent systems used for the treatment of homogeneous catalyzed reaction effluents after a product/catalyst separation zone related to the removal of heavy by-products. The amount of nonpolar solvent employed in the liquid-liquid separation zone should be sufficiently controlled to obtain, by phase separation, two immiscible liquid phases depicted by regions 2, 4 and 6 of FIG. 1 comprising a polar phase and a nonpolar phase and to prevent or minimize formation of three immiscible liquid phases depicted by region 5 of FIG. 1 and one homogeneous liquid phase depicted by regions 1, 3 and 7 of FIG. 1. In general, the amount of nonpolar solvent employed may range from about 5 percent by weight or less up to about 95 percent by weight or more based on the total weight of the reaction mixture.

Illustrative nonpolar reaction and extraction solvents useful in some embodiments of the present invention include, for example, propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diusobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, dodecene, tetradecene, and heptadecanal. For some embodiments of the present invention, the one or more by-products or unreacted olefin (fresh or recycled) may serve as the nonpolar reaction solvent. Some embodiments of the present invention may involve recovering and recycling unconverted olefin (optionally with hydrocarbons from the feed or from inadvertent hydrogenation during the hydroformylation process) as a portion of the non-polar solvent. The solubility parameters of illustrative nonpolar solvents that can be used in some embodiments are given in Table 1 below.

TABLE 1

Solubility Parameters of Illustrative Non-Polar Solvents

| Non-Polar Solvent | δSolvent (cal/cm 3) $^{1/2}$ | δSolvent (kJ/m 3) $^{1/2}$ |
|---|---|---|
| Propane | 5.76 | 373 |
| 2,2-Dimethylpropane | 6.10 | 395 |
| Butane | 6.58 | 426 |
| 2,2-Dimethylbutane | 6.69 | 433 |
| Pentane | 7.02 | 454 |
| Isopropyl Ether | 7.06 | 457 |
| Hexane | 7.27 | 470 |
| Triethylamine | 7.42 | 480 |
| Heptane | 7.50 | 485 |
| Octane | 7.54 | 488 |
| Nonane | 7.64 | 494 |
| Decane | 7.72 | 499 |
| Isobutyl Isobutyrate | 7.74 | 501 |
| Tributylamine | 7.76 | 502 |
| Undecane | 7.80 | 505 |
| 2,2,4-Trimethylpentyl Acetate | 7.93 | 513 |
| Isobutyl Heptyl Ketone | 7.95 | 514 |
| Diisobutyl Ketone | 8.06 | 521 |
| Cyclopentane | 8.08 | 523 |
| Cyclohexane | 8.19 | 530 |
| n-Nonylbenzene | 8.49 | 549 |
| n-Octylbenzene | 8.56 | 554 |
| n-Butylbenzene | 8.57 | 554 |
| p-Xylene | 8.83 | 571 |
| Ethylbenzene | 8.84 | 572 |
| 1,3,5-Trimethylbenzene | 8.84 | 572 |
| m-Xylene | 8.88 | 574 |
| Toluene | 8.93 | 578 |
| o-Xylene | 9.06 | 586 |

As known to those having ordinary skill in the art, hydroformylation processes can result in the generation of undesired heavies or heavy byproducts. In embodiments of the present invention, the undesired heavies can be selectively removed by extraction and phase separation in a nonpolar extraction solvent. As indicated above, the processes of this invention are conducted in the presence of one or more nonpolar solvents and one or more polar solvents, or in the presence of one or more nonpolar solvents followed by mixing with one or more polar solvents, or in the presence of one or more polar solvents followed by mixing with one or more nonpolar solvents. The undesired heavies are preferably extracted from the reaction product fluid through the use of an appropriate nonpolar extraction solvent such that any extraction of the one or more reactants, metal-organophosphorus ligand complex catalyst, and optionally free organophosphorus ligand from the reaction product fluid is minimized or eliminated. The one or more reactants, metal-organophosphorus ligand complex catalyst, and optionally free organophosphorus ligand is preferably retained in the reaction product fluid through the use of an appropriate polar extraction solvent such that the extraction of the undesired heavies product from the reaction product fluid is maximized. In some embodiments, the polar solvent is an aqueous mixture preferably containing up to about 30 to 40 weight percent water. In other embodiments, the polar solvent is an aqueous mixture containing up to about 10 weight percent water. Depending on the particular undesired heavies, suitable polar reaction and extraction solvents include, for example, lactones, nitriles, alkanols, cyclic acetals, pyrrolidones, formamides, sulfoxides, water and the like. In some embodiments, the polar solvent is not a combination of a primary alkanol and water as primary alkanols are not desirable for this process.

Mixtures of one or more different polar solvents may be employed if desired. In some embodiments, the Hildebrand solubility parameter for the polar solvent or mixtures of one or more different polar solvents may be less than about 13.5 $(cal/cm^3)^{1/2}$ or 873 $(KJ/m^3)^{1/2}$, preferably less than about 13.0 $(cal/cm^3)^{1/2}$ or 841 $(KJ/m^3)^{1/2}$, and more preferably less than about 12.5 $(cal/cm^3)^{1/2}$ or 809 $(KJ/m^3)^{1/2}$. The amount of polar and/or nonpolar solvent employed in the reaction zone, if any, is not critical to the subject invention and need only be that amount sufficient to provide the reaction medium with the particular metal concentration desired for a given process. The amount of polar solvent employed in the liquid-liquid separation zone is not critical to the subject invention and need only be that amount sufficient to facilitate the extraction of the one or more heavy by-products from the reaction product fluid for any given process while minimizing the ligand and rhodium losses. The amount of polar solvent employed in the liquid-liquid separation zone should be sufficiently controlled to obtain, by phase separation, two immiscible liquid phases comprising a polar phase and a nonpolar phase depicted by regions 2, 4 and 6 of FIG. 1 and to prevent or minimize formation of three immiscible liquid phases depicted by region 5 of FIG. 1 and one immiscible liquid phase depicted by regions 1, 3 and 7 of FIG. 1. In general, the amount of polar solvent employed may range from about 5 percent by weight or up to about 50 percent by weight based on the total weight of the reaction product fluid.

Illustrative polar reaction and extraction solvents useful in embodiments of the present invention can include, for example, propionitrile, 1,3-dioxolane, 3-methoxypropionitrile, N-methylpyrrolidone, N,N-dimethylformamide, 2-methyl-2-oxazoline, adiponitrile, acetonitrile, epsilon caprolactone, glutaronitrile, 3-methyl-2-oxazolidinone, water, dimethyl sulfoxide and sulfolane. In some embodiments, one or more hydroformylation reaction products may serve as the polar solvent. The solubility parameters of illustrative polar solvents are given in Table 2.

TABLE 2

Solubility Parameters of Illustrative Polar Solvents

| Polar Solvent | δSolvent $(cal/cm\ 3)^{1/2}$ | δSolvent $(kJ/m\ 3)^{1/2}$ |
|---|---|---|
| Propionitrile | 10.73 | 694 |
| 1,3-Dioxolane | 11.33 | 733 |
| 3-Methoxypropionitrile | 11.37 | 735 |
| N-Methylpyrrolidone | 11.57 | 748 |
| N,N-Dimethylformamide | 11.76 | 761 |
| 2-Methyl-2-Oxazoline | 12.00 | 776 |
| Adiponitrile | 12.05 | 779 |
| Acetonitrile | 12.21 | 790 |
| E-Caprolactone | 12.66 | 819 |
| Sulfolane | 12.80 | 828 |
| Glutaronitrile | 13.10 | 847 |
| Dimethyl Sulfoxide | 13.10 | 847 |
| 3-Methyl-2-Oxazolidinone | 13.33 | 862 |
| Water | 23.53 | 1522 |

Extraction to obtain one phase comprising the one or more reactants, metal-monophosphite ligand complex catalyst, optionally free monophosphite ligand and nonpolar or polar solvent and at least one other phase comprising one or more heavy by-products and polar or nonpolar solvent is an equilibrium process. The relative volumes of the polar solvent and the nonpolar solvent or reaction product fluid in this extraction operation are determined in part by the solubility of the one or more reactants, metal-monophosphite ligand complex catalyst, optionally free monophosphite ligand and one or more products in the solvents used, and the amount of undesired heavies to be extracted. For example, if the heavies to be extracted show high solubility in the polar or nonpolar solvent and are present at a relatively low concentration in the reaction product fluid, it is possible to extract the heavies by using the polar or nonpolar solvent in a relatively small volume ratio relative to the reaction product fluid. The polar and nonpolar solvents described above may be used as extraction solvents. As described herein, both a polar and a non-polar solvent are present in the liquid-liquid separation zone.

In general, there is little benefit in employing a temperature higher than the hydroformylation reaction temperature in the extraction and phase separation process (a liquid-liquid separation), and desirable results can be obtained by employing an extraction temperature lower than the hydroformylation reaction temperature. The extraction is when both polar solvent and nonpolar solvent are mixed and the components of the hydroformylation reaction product fluid separate into the different phases, and the phase separation phase is when the polar phase is separated from the nonpolar phase. Depending on the particular process, phase separation temperatures may range from about −80° C. or less to about 200° C. or greater, preferably between 0° C. to 70° C. and most preferably 25 to 50° C. Regarding pressure, in general, there is little benefit in conducting the extraction and phase separation at elevated pressure other than to avoid degassing of fluid; the extraction, however, can be conducted at elevated pressure if desired to keep gases dissolved. The temperature and pressure employed in the separation zone should be sufficiently controlled to obtain by phase separation two immiscible liquid phases comprising a polar phase and a nonpolar phase depicted by regions 2, 4 and 6 of FIG. 1 and to prevent or minimize formation of three immiscible liquid phases depicted by region 5 of FIG. 1 and one immiscible liquid phase depicted by regions 1, 3 and 7 of FIG. 1.

The time for mixing the reaction product fluid with the polar or nonpolar solvent (i.e., the time before the phase separation) depends on the rate until the two phases reach the equilibrium condition. Generally, such a time can vary from within one minute or less to a longer period of one hour or more depending, for example, on the particular components in the reaction product fluid and the solvents used.

Embodiments of the present invention utilize a compound according to Formula (I) in a hydroformylation process:

(I)

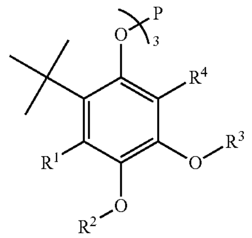

wherein $R^1$-$R^4$ are the same or different and each individually represent an hydrogen, a monovalent hydrocarbyl or substituted hydrocarbyl radical selected from alkyl, arylalkyl, and alicyclic radicals. In some embodiments, $R^1$ and $R^2$ may be linked to form cyclic moieties. In some embodiments, $R^2$ and $R^3$ may be linked to form cyclic moieties. In some embodiments, $R^3$ and $R^4$ may be linked to form cyclic moieties. Such compounds can advantageously be used as a monophosphite ligand in a transition metal complex hydroformylation catalytic precursor composition according to some embodiments of the present invention as well as in a metal-monophosphite ligand complex catalyst in processes (e.g., processes for separating one or more heavies from a hydroformylation reaction product fluid and hydroformylation processes) according to some embodiments of the present invention. Additional information regarding the compounds according to formula (I) is provided in the discussion below regarding its use as a ligand and it may be referred to as the monophosphite ligand according to formula (I).

Some embodiments of the present invention relate to transition metal complex hydroformylation catalytic precursor compositions that consist essentially of a solubilized Group VIII transition metal-monophosphite complex, an organic solvent, and free monophosphite ligand, wherein the monophosphite ligand of the metal-monophosphite complex and the free monophosphite ligand are each a compound according to formula (I). In some embodiments, the monophosphite ligand of the metal-monophosphite complex and the free monophosphite ligand are the same compound according to formula (I).

The metal-monophosphite ligand complex catalysts useful in processes of the present invention comprise a catalytic metal. The catalytic metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium.

The number of available coordination sites on such metals is well known in the art. Thus the catalytic species, which may comprise a complex catalyst mixture, may comprise monomeric, dimeric or higher nuclearity forms, which are preferably characterized by at least one monophosphite-containing molecule (e.g., a compound according to formula (I)) complexed per one molecule of metal, e.g., rhodium. For instance, it is considered that the catalytic species of the preferred catalyst employed in a hydroformylation reaction may be complexed with carbon monoxide and hydrogen in addition to the monophosphite ligands according to formula (I) in view of the carbon monoxide and hydrogen gas employed by the hydroformylation reaction.

Illustrative metal-monophosphite ligand complex catalysts employable in such hydroformylation reactions encompassed by this invention include metal-monophosphite ligand complex catalysts using compounds according to formula (I). Such catalysts can be prepared using techniques known to those of skill in the art based on the teachings herein. In general, such catalysts may be preformed or formed in situ and consist essentially of metal in complex combination with a monophosphite ligand according to formula (I). It is believed that carbon monoxide is also present and complexed with the metal in the active species. The active species may also contain hydrogen directly bonded to the metal.

The term "complex" as used herein means a coordination compound formed by the union of one or more electronically rich molecules or atoms capable of independent existence with one or more electronically poor molecules or atoms, each of which is also capable of independent existence. For example, the monophosphite ligands according to formula (I) possess a phosphorus donor atom having one available or unshared pair of electrons that are capable of forming a coordinate bond independently or possibly in concert (e.g., via chelation) with the metal. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and RP(O)(OH)O (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2{=}CHCH_2$, $CH_3CH{=}CHCH_2$, $C_6H_5CN$, $CH_3CN$, $NH_3$, pyridine, $(C_2H_5)_3N$, mono-olefins, diolefins and triolefins, tetrahydrofuran, and the like. The complex species are preferably free of any additional organic ligand or anion that might poison the catalyst or have an undue adverse effect on catalyst performance. It is preferred in the metal-monophosphite ligand complex catalyzed hydroformylation reactions that the active catalysts be free of halogen and sulfur directly bonded to the metal, although such may not be absolutely necessary.

As noted above, triorganophosphites that may serve as the monophosphite ligand of the metal-monophosphite ligand complex catalyst and/or free ligand include those according to formula (I):

(I)

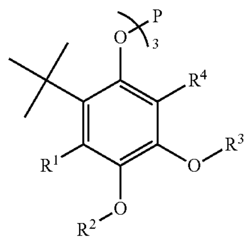

wherein $R^1$-$R^4$ are the same or different and each individually represent an hydrogen, a monovalent hydrocarbyl or substituted hydrocarbyl radical selected from alkyl, arylalkyl, and alicyclic radicals. In some embodiments, $R^1$ and $R^2$ may be linked to form cyclic moieties. In some embodiments, $R^2$ and $R^3$ may be linked to form cyclic moieties. In some embodiments, $R^3$ and $R^4$ may be linked to form cyclic moieties.

Any of the $R^{1-4}$ radicals of such monophosphites according to formula (I) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, arylalkyl, alkaryl and cyclohexyl substituents, may include for example alkylethers, polyether radicals such as $—O(CH_2CH_2)_yOR^5$, alkylamines, dialkylamines, acyl radicals such as $—C(O)\ R^5$ acyloxy radicals such as $—OC(O)\ R^5$; amido radicals such as $—CON(R^5)_2$ and $—N(R^5)COR^5$; sulfonyl radicals such as $—SO_2R^5$, alkoxy radicals such as $—OR^5$; sulfinyl radicals such as $—SOR^5$, phosphonyl radicals such as $—P(O)(R^5)_2$, as well as halo, nitro, cyano, trifluoromethyl, hydroxy radicals, and the like, wherein y is 1 to 20 and wherein each $R^5$ radical individually represents the same or different monovalent hydrocarbon radical having from 1 to 18 carbon atoms (e.g., alkyl, aryl, arylalkyl, alkaryl and cyclohexyl radicals), with the proviso that in amido substituents such as $—C(O)N(R^5)_2$ and $—N(R^5)\ COR^5$ each $R^5$ bonded to N can also be hydrogen. Any of the substituted or unsubstituted hydrocarbon radicals groups that make up a particular given monophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl and the like; arylalkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, $—OCH_2\ CH_2\ OCH_3$, $—O(CH_2CH_2)_2OCH_3$, $—O(CH_2\ CH_2)_3OCH_3$, and the like; aryloxy radicals such as phenoxy and the like; as well as amino radicals such as $—NH_2$, $—N(CH_3)_2$, $—NHCH_3$, $—NH(C_2H_5)$, and the like; acyl radicals such as $—C(O)CH_3$, $—C(O)C_2H_5$, $—C(O)C_6H_5$, and the like; carbonyloxy radicals such as $—C(O)OCH_3$ and the like; oxycarbonyl radicals such as $—O(CO)C_6H_5$, and the like; amido radicals such as $—CONH_2$, $—CON(CH_3)_2$, $—NHC(O)CH_3$, and the like; sulfonyl radicals such as $—S(O)_2C_2H_5$ and the like; sulfinyl radicals such as $—S(O)CH_3$ and the like; sulfidyl radicals such as $—SCH_3$, $—SC_2H_5$, $—SC_6H_5$, and the like; phosphonyl radicals such as $—P(O)(C_6H_5)_2$, $—P(O)(CH_3)_2$, $—P(O)(C_2H_5)_2$, $—P(O)(C_3H_7)_2$, $—P(O)(C_4H_9)_2$, $—P(O)(C_6H_{13})_2$, $—P(O)CH_3(C_6H_5)$, $—P(O)(H)(C_6H_5)$, and the like.

Some typical examples of monophospite ligands according to formula (I) according to some embodiments of the present invention include:

Ligand A

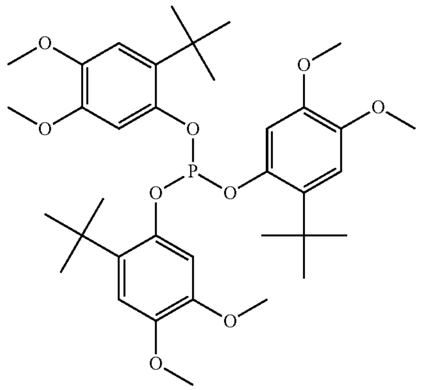

Ligand B

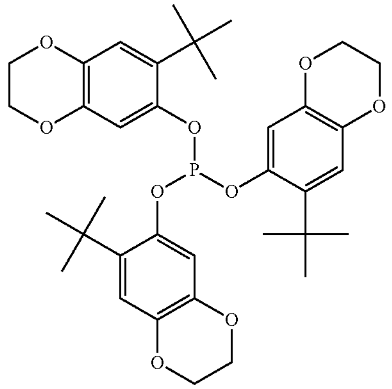

Ligand C

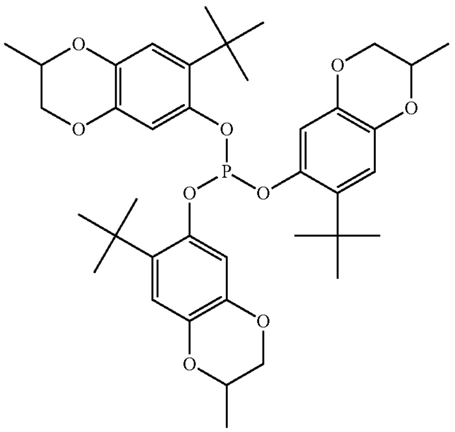

Ligand D

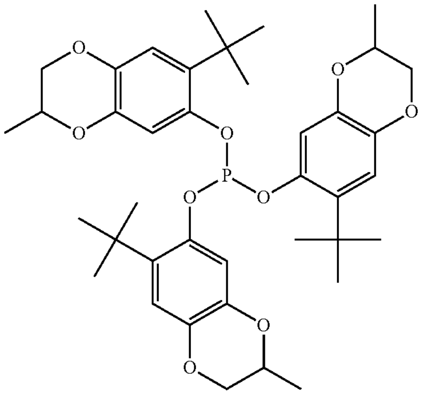

-continued

Ligand E

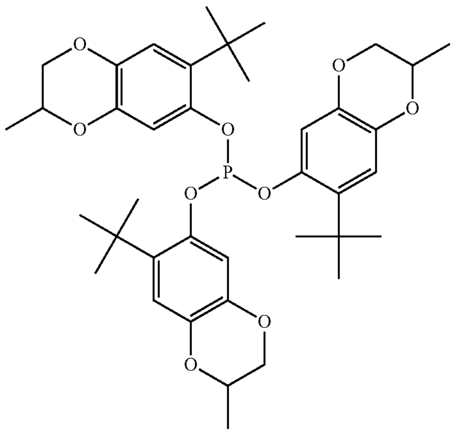

Ligand F

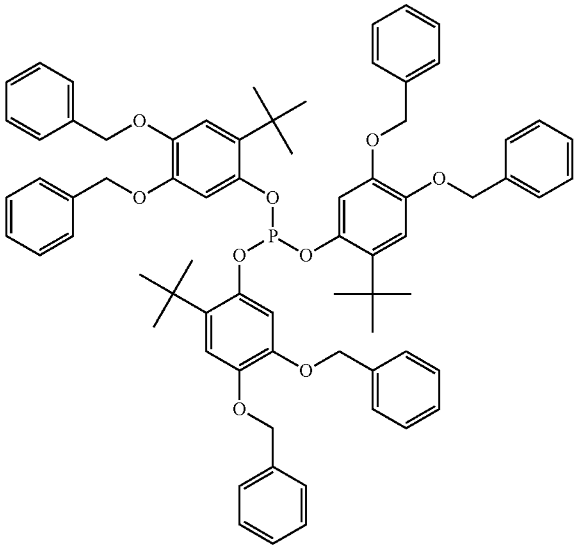

Ligand G

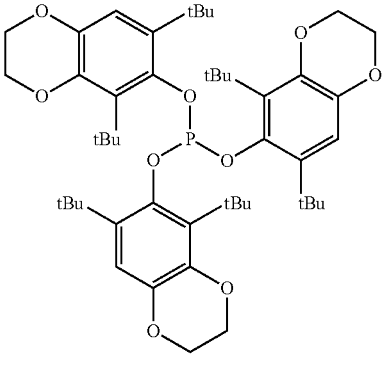

-continued

Ligand H

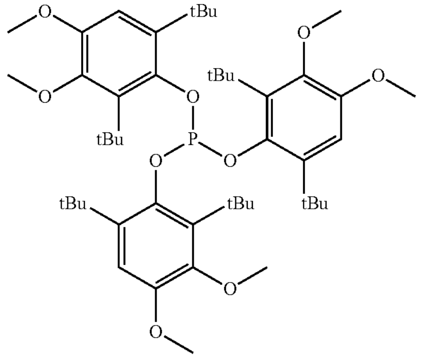

Ligand I

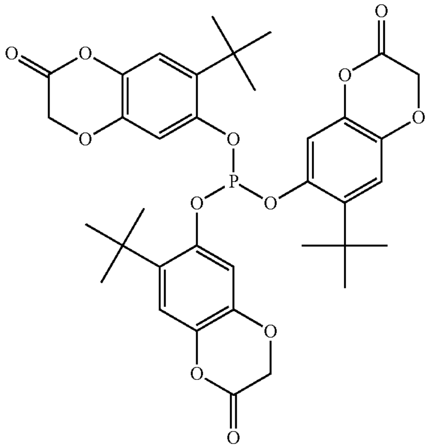

Ligand J

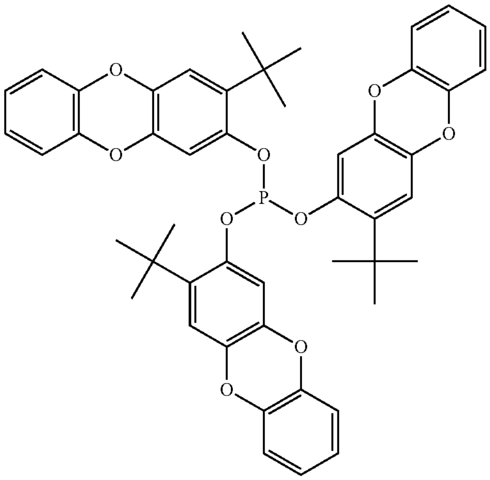

As noted above, the metal-monophosphite ligand complex catalysts may be formed by methods known in the art based on the teachings herein. The metal-monophosphite ligand complex catalysts may be in homogeneous or heterogeneous form. For instance, preformed rhodium hydridocarbonyl-monophosphite ligand catalysts may be prepared and introduced into the reaction mixture of a hydroformylation process. More preferably, the rhodium-monophosphite ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with a monophosphite ligand according to formula (I) for the in situ formation of the active catalyst. In some embodiments, rhodium dicarbonyl acetylacetonate can be employed as a rhodium precursor and reacted in the presence of a solvent with a monophosphite ligand according to formula (I) to form a catalytic rhodium-monophosphite ligand complex precursor that is introduced into the reactor along with excess (free) monophosphite ligand for the in situ formation of the active catalyst. In any event, it is sufficient for the purposes of this invention that carbon monoxide, hydrogen and the monophosphite ligand according to formula (I) are all ligands that are capable of being complexed with the metal and that an active metal-monophosphite ligand catalyst complex is present in the reaction mixture under the conditions used in the hydroformylation reaction. Carbonyl and the monophosphite ligands, if not already complexed with the initial rhodium, may be complexed to the rhodium either prior to or in situ during the hydroformylation process.

By way of illustration, a transition metal complex hydroformylation catalyst precursor composition consists essentially of a solubilized rhodium carbonyl monophosphite ligand complex precursor, a solvent and, optionally, free monophosphite ligand, wherein the monophosphite ligand is a compound according to formula (I). The catalyst precursor composition can be prepared by forming a solution of rhodium dicarbonyl acetylacetonate, an organic solvent and a monophosphite ligand according to formula (I). The monophosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium monophosphite ligand complex precursor are soluble can be employed. The amounts of rhodium complex catalyst precursor, organic solvent and monophosphite ligand, as well as their preferred embodiments present in such catalyst precursor compositions may correspond to those amounts employable in the hydroformylation process of this invention. Experience has shown that the acetylacetonate ligand of a precursor catalyst is replaced after the hydroformylation process has begun with a different ligand, e.g., hydrogen, carbon monoxide or monophosphite ligand, to form the active complex catalyst as explained above. The acetylacetone that is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphite ligand complex catalyst used in processes of the present invention consists essentially of the metal (e.g., rhodium) complexed with carbon monoxide and a monophosphite ligand according to formula (I), said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the monophosphite ligand. Further, such terminology does not exclude the possibility of other organic ligands and/or anions that might also be complexed with the metal. Materials in amounts that unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-monophosphite ligand complex catalyst may be present as a result of being ligands bound to a precursor catalyst and/or as a result of in situ formation, e.g., due to the hydrogen and carbon monoxide gases employed in hydroformylation process.

As noted, hydroformylation processes according to embodiments of the present invention involves the use of a metal-monophosphite ligand complex catalyst as described herein. Mixtures of such catalysts can also be employed if desired. The amount of metal-monophosphite ligand complex catalyst present in the reaction fluid of a given hydroformylation process encompassed by this invention need only be that minimum amount necessary to provide the given metal concentration desired to be employed and that will furnish the basis for at least the catalytic amount of metal necessary to catalyze the particular hydroformylation process involved. In general, catalytic metal (e.g., rhodium) concentrations in the range of from 5 ppmw to 1000 ppmw, calculated as free metal in the reaction medium, should be sufficient for most processes, while it is generally preferred to employ from 10 to 500 ppmw of metal, and more preferably from 25 to 350 ppmw of metal. Analytical techniques for measuring catalytic metal concentrations are well known to the skilled person, and include atomic absorption (AA), inductively coupled plasma (ICP) and X-ray fluorescence (XRF); AA is typically preferred.

In addition to the metal-monophosphite ligand complex catalyst, free monophosphite ligand according to formula (I) (i.e., ligand that is not complexed with the metal) may also be present in the reaction medium. The free monophosphite ligand may correspond to any of the above-defined monophosphite ligands according to formula (I) discussed above as employable herein. It is preferred that the free monophosphite ligand be the same as the monophosphite ligand of the metal-monophosphite ligand complex catalyst employed. However, such ligands need not be the same in any given process. The hydroformylation process may involve from 0.1 moles or less to 200 moles or higher of free monophosphite ligand of formula (I) per mole of metal in the reaction medium. Preferably, the hydroformylation process is carried out in the presence of from 1 to 100 moles of free monophosphite ligand of formula (I) per mole of metal present in the reaction medium. Said amounts of monophosphite ligand are the sum of both the amount of monophosphite ligand that is bound (complexed) to the metal present and the amount of free (non-complexed) monophosphite ligand present. If desired, make-up or additional monophosphite ligand according to formula (I) can be supplied to the reaction medium of the hydroformylation process at any time and in any suitable manner, e.g. to maintain a predetermined level of free ligand in the reaction medium.

The use of an optional aqueous buffer solution to prevent and/or lessen hydrolytic degradation of an organophosphite ligand and deactivation of a metal-organophosphite ligand complex is disclosed in U.S. Pat. Nos. 5,741,942 and 5,741,944 which employ aqueous buffers which are generally Group 1 or 2 metal (Na, K, Ca, etc.) salts of weak acids.

Some embodiments of the present invention relate to hydroformylation processes that utilize monophosphite ligands according to formula (I).

In one embodiment, a process for separating one or more heavies from a hydroformylation reaction product fluid comprising a metal-monophosphite ligand complex catalyst, optionally free monophosphite ligand, one or more aldehyde products, and heavies, comprises:

(a) hydroformylating a $C_6$ to $C_{40}$ mono-olefin with the metal-monophosphite ligand complex catalyst and optionally free monophosphite ligand in a reaction zone to provide a hydroformylation reaction product fluid, wherein the monophosphite ligand comprises a compound according to formula (I):

(I)

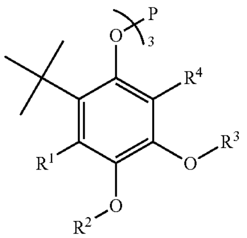

wherein $R^1$-$R^4$ are the same or different and each individually represent an hydrogen, a monovalent hydrocarbyl or substituted hydrocarbyl radical selected from alkyl, arylalkyl, and alicyclic radicals;

(b) removing a portion of the hydroformylation reaction product fluid from the reaction zone and transferring the portion to a product/catalyst separation zone wherein a portion of the aldehyde products are vaporized as an overhead stream and wherein a non-volatilized catalyst fluid comprising the metal-monophosphite ligand complex catalyst is recovered as a bottoms stream;

(c) mixing at least a portion of the bottoms stream obtained in step (b) in the presence of a nonpolar solvent and a polar solvent to obtain, by phase separation, two phases: a first phase comprising the polar solvent, the metal-monophosphite ligand complex catalyst and optionally free monophosphite ligand, and a second phase comprising the non-polar solvent, a portion of the heavies, and at least a portion of the remaining aldehyde products; and (d) recovering said metal-monophosphite ligand complex catalyst and at least a portion of any free monophosite ligand from the first phase and returning the recovered metal-monphosphite ligand complext catalyst and any recovered free monophosphite ligand to the reaction zone.

In some embodiments, a hydroformylation process for producing aldehydes comprises reacting an olefinically unsaturated compound selected from the group consisting of alpha-olefins containing from 6 to 40 carbon atoms, internal olefins containing from 6 to 20 carbon atoms, and mixtures of such alpha and internal olefins with carbon monoxide and hydrogen in a reaction zone in the presence of a rhodium-monophosphite complex catalyst consisting essentially of rhodium complexed with carbon monoxide and at least one monophosphite ligand, wherein the at least one monophosphite ligand is a compound according to formula (I):

(I)

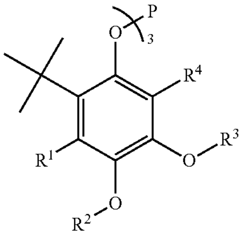

wherein $R^1$-$R^4$ are the same or different and each individually represent an hydrogen, a monovalent hydrocarbyl or substituted hydrocarbyl radical selected from alkyl, arylalkyl, and alicyclic radicals.

The hydroformylation products may be asymmetric, non-asymmetric or a combination thereof, with the preferred products being non-asymmetric. The process may be conducted in any batch, continuous or semi-continuous fashion and may involve any catalyst liquid and/or gas recycle operation desired.

The recycle procedure generally involves withdrawing a portion of the liquid reaction medium containing the catalyst and aldehyde product (reaction product fluid) from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. In one embodiment, a vaporizer and a membrane separation process can be used in series or in parallel to effect the product/catalyst separation. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired. For the purposes of this disclosure, the product/catalyst separation zone encompassing vaporizer and/or a membrane separation processes may also be referred to as the "vaporization zone" since vaporization is the more common method. The majority of the product from the hydroformylation process is recovered by use of this product/catalyst separation zone. Other product recoveries such as from reactor vent condensors and downstream heavies recovery or cracking operations are considered separately.

In some embodiments, the hydroformylation reaction product fluid employable herein includes any fluid derived from any corresponding hydroformylation process that contains at least some amount of five different main ingredients or components, i.e., the aldehyde product, a metal-monophosphite ligand (according to formula (I)) complex catalyst, free monophosphite ligand according to formula (I), an organic solubilizing agent for said catalyst and said free ligand, and heavies which may contribute or eventually comprise a large portion (or all) of the organic solubilizing agent, said ingredients corresponding to those employed and/or produced by the hydroformylation process from whence the hydroformylation reaction product fluid may be derived. The hydroformylation reaction product fluids employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products ("heavies"), as well as other inert co-solvent type materials or hydrocarbon additives, if employed.

The reaction conditions of the hydroformylation process encompassed by embodiments of the present invention may include any suitable hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformylation process of this invention is preferably from 1 to 6,900 kPa, and more preferably from 21 to 5,500 kPa, while the hydrogen partial pressure is preferably from 34 to 3,400 kPa and more preferably from 69 to 2,100 kPa.

In general, the hydroformylation process may be conducted at any operable reaction temperature. Advantageously, the hydroformylation process is conducted at a reaction temperature from −25° C. to 200° C. In general, hydroformylation reaction temperatures of 50° C. to 120° C. are preferred for all types of olefinic starting materials. It is to be understood that when non-optically active aldehyde products are desired, achiral type olefin starting materials and organophosphorous ligands are employed and when optically active aldehyde products are desired prochiral or chiral type olefin starting materials and organophosphorous ligands are employed. The hydroformylation reaction conditions employed will be governed by the type of aldehyde product desired.

The hydroformylation process of this invention may be carried out using one or more suitable reactors such as, for example, a fixed bed reactor, a fluid bed reactor, a tubular reactor, a venturi reactor, a bubble column reactor, a continuous stirred tank reactor (CSTR) or a slurry reactor. The optimum size and shape of the reactor will depend on the type of reactor used. The at least one reaction zone employed in this invention may be a single vessel or may comprise two or more discrete vessels. The at least one liquid-liquid separation zone employed in this invention may be a single vessel or may comprise two or more discrete vessels. The optional at least one buffer treatment zone which can be employed in some embodiments of the present invention as taught in U.S. Pat. No. 5,741,944 may be a single vessel or may comprise two or more discreet vessels. The reaction zone(s), product/catalyst separation zone(s), and liquid-liquid separation zone(s) employed herein may exist in the same vessel or in different vessels. For example, reactive separation techniques such as reactive distillation, reactive membrane separation and the like may occur in the reaction zone(s).

Hydroformylation processes of the present invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the process especially to maintain the desired molar ratio of the starting materials. The reaction steps may be effected by the incremental addition of one of the starting materials to the other. Also, the reaction steps can be combined by the joint addition of the starting materials. The starting materials may be added to each or all the reaction zones in series. When complete conversion is not desired or not obtainable, the starting materials can be separated from the product, for example by distillation, and the starting materials then recycled back into the reaction zone. Such types of recycle procedures are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. A particularly desirable hydroformylation process of this invention is a continuous liquid catalyst recycle process. Suitable liquid catalyst recycle procedures are disclosed, for example, in U.S. Pat. Nos. 4,668,651; 4,774,361; 5,102,505 and 5,110,990.

Such hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of the present invention may be conducted in one or more steps, zones, or stages. The exact number of reaction steps, zones, or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In some embodiments, hydroformylation processes of the present invention may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel can be a cost effective way of using the reactor vessel volume. It can significantly reduce the number of vessels that otherwise would be required to achieve the same results. Fewer vessels reduces the overall capital required and maintenance concerns with separate vessels and agitators.

As indicated above, it is generally preferred to carry out the hydroformylation processes of the present invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. In accordance with embodiments of the present invention, the organophosphorous ligand is a monophosphite ligand according to formula (I). The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s).

In some embodiments of the present invention, the aldehyde product mixtures are be separated from the other components of the hydroformylation reaction product fluid in which the aldehyde mixtures are produced in a product/catalyst separation zone. Suitable product/catalyst separation methods include, for example, distillation, vaporization, wiped film evaporation, falling film evaporation, membranes, and the like or any combination thereof.

As indicated above, at the conclusion of (or during) the process of this invention, the desired aldehydes may be recovered from the hydroformylation reaction product fluid used in the process of this invention. For example, the recovery techniques disclosed in U.S. Pat. Nos. 4,148,830 and 4,247,486 can be used. For instance, in a continuous liquid catalyst recycle process the portion of the hydroformylation reaction product fluid (containing aldehyde product, catalyst, etc.), i.e., reaction fluid, removed from the reaction zone can be passed to a product/catalyst separation zone, e.g., vaporizer/separator, wherein the desired aldehyde product can be separated via distillation, in one or more stages, under normal, reduced or elevated pressure, from the reaction product fluid, condensed and collected in a product receiver, and further purified if desired. The remaining non-volatilized catalyst containing liquid reaction mixture (a bottoms stream) may then be recycled back to the reactor as may if desired any other volatile materials, e.g., unreacted olefin, together with any hydrogen and carbon monoxide dissolved in the bottoms stream after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the monophosphite ligand and reaction products. When an alpha-mono-olefin reactant is also employed, the aldehyde derivative thereof can also be separated by the above methods.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_6$) are involved or under vacuum when high boiling aldehydes (e.g. $C_7$ or greater) are involved. For instance, a common practice is to subject the reaction product fluid removed from the hydroformylation reactor to a pressure reduction so as to volatilize a substantial portion of the unreacted gases dissolved in the reaction product fluid and then provide the reaction product fluid to the product/catalyst separation zone, e.g. vaporizer/separator, wherein the desired aldehyde product is distilled. In general, distillation pressures ranging from vacuum pressures on up to total gas pressure of 340 kPa should be sufficient for most purposes.

Recent improvements for hydroformylation processes with phosphite-based catalysts use stripping gas vaporizers such as disclosed in WO1997007086, WO2010003073, WO2016089602 and WO2020240194. These processes can increase the amount of heavies that are also removed during the vaporization process while reducing catalyst losses. However, as the desired aldehyde product in embodiments of the present invention exceeds $C_6$ aldehydes, the ability of such strip gas vaporizers to remove heavies at their rate of formation may be limited.

In a process separate from the product/catalyst separation process described above, in some embodiments of the present invention, a portion of the catalyst containing residue (e.g., bottoms stream from a vaporizer) or membrane retentate can be treated to a phase separation process wherein the catalyst and catalyst components are separated from at least some of the heavies. By inducing a phase separation, a partition of materials can be obtained wherein the partition coefficients of the catalyst and heavies are sufficiently different to effect a suitable removal of heavies with minimal catalyst losses.

Phase separation processes for hydroformylation fluids are known and in general are preferably performed under inert atmosphere and in suitable equipment such as glass lined, stainless steel or similar type equipment. The extraction and phase separation steps (liquid-liquid separation) of some embodiments of the present invention may be conducted in one or more stages. The extraction system preferably has greater than one theoretical stage of extraction both above and below the entry point of the residue from the product/catalyst separation zone. The exact number of stages will be governed by the best compromise between capital costs, equipment footprint, and desire for high extraction efficiency and ease of operation. The extraction process can be conducted continuously or in a batch mode. When conducted continuously, the process may be in a co-current, counter-current, or fractional countercurrent.

Once the aldehyde product stream has been separated from the residual catalyst solution (the bottoms stream from the product/catalyst separation zone), the bottoms stream can be phase separated in the presence of a nonpolar solvent and a polar solvent to provide two phases: a first phase comprising the polar solvent, the metal-monophosphite ligand complex catalyst and optionally free monophosphite ligand, and a second phase comprising the non-polar solvent, a portion of the heavies, and at least a portion of the remaining aldehyde products. The choice of polar and nonpolar solvents will depend on the polarity of the catalyst and catalyst components and the polarity of the heavies. In general, with high molecular weight, single functionality aldehydes, the resulting heavies will tend to be nonpolar in which case it is preferred that the ligand and the catalyst have higher polarity. The polarity (as described as a solubility parameter) of the ligand and the heavy trimer from a C9 linear aldehyde can be anticipated by using group contribution approach theory as described in U.S. Pat. No. 5,932,772. In order to effect an efficient separation of these two compounds, it is believed that a difference in the calculated polarity of at least 0.5 is necessary, prefereably 1 and even more preferably 1.5. Using this approach, the following calculated polarities can be determined:

Tables 3A and 3B—Representative Calculated Solubility Parameters for Ligands Compared to Examples of Heavies

| | Calculated polarity |
|---|---|
| Control: Tris(2,4-ditertbutylphenyl)phosphite | 8.25 |
| Ligand A of the invention | 9.97 |
| Ligand B of the invention | 10.96 |
| Ligand C of the invention | 10.50 |
| Ligand D of the invention | 10.50 |
| Ligand E of the invention | 10.50 |
| Ligand F of the invention | 10.61 |
| Ligand G of the invention | 10.00 |
| Ligand H of the invention | 9.33 |
| Ligand I of the invention | 12.11 |
| Ligand J of the invention | 16.45 |

| Heavies Compound | Typical structure | Calculated polarity |
|---|---|---|
| C4 Aldehyde trimer | 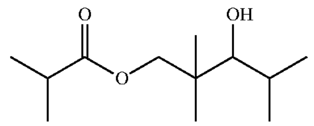 | 8.78 |
| C6 Aldehyde trimer | 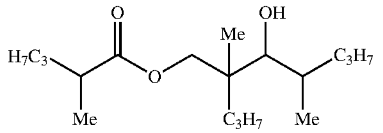 | 8.55 |
| C9 Aldehyde trimer | 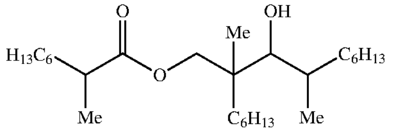 | 8.38 |

As can be seen here, the model $C_9$ heavy, nonanal trimer, has virtually the same solubility parameter as the Control ligand (Tris(2,4-ditertbutylphenyl)phosphite); thus, a phase separation process would not be effective in separating these heavies from the corresponding ligand or the corresponding rhodium catalyst. However, inventive Ligands A-J (compounds (monophosphite ligands) according to Formula (I)) exhibit well over a 1.0 difference between its solubility parameter and solubility parameter of the heavy by-product such that good phase separation is anticipated.

One approach for determining suitable polar and nonpolar solvents for using phase separation to remove heavies is to select solvents that provide a desirable partition coefficient for heavies while minimizing catalyst and catalyst component (e.g., monophosphite ligand) losses. For example, a polar solvent and nonpolar solvent can be selected and then the concentration of heavies in each phase can be measured by gas chromatography using techniques known to those of ordinary skill in the art. A partition coefficient of the heavies after extraction can be defined as $K_{p1}$:

$$Kp1 = \frac{\text{Concentration of Heavies in polar phase}}{\text{Concentration of Heavies in nonpolar phase}}$$

In some embodiments, the polar solvent and non-polar solvent are selected to provide a partition coefficient ($K_{p1}$) of 0.5 or less. In some embodiments, the polar solvent and non-polar solvent are selected to provide a partition coefficient ($K_{p1}$) of 0.2 or less. In some embodiments, the polar solvent and non-polar solvent are selected to provide a partition coefficient ($K_{p1}$) of 0.1 or less. Low $K_{p1}$ values will have the heavies preferentially distribute into the non-polar phase.

As suggested above, another important factor in selecting polar and nonpolar solvents for phase separation is for the rhodium to phase separate into the polar phase (away from the heavies). In other words, some embodiments of the present invention are aimed at removing heavies without rhodium loss. Thus, while the partition coefficient for heavies ($K_{p1}$) should be low for a given combination of polar and nonpolar solvent, a partition coefficient for rhodium ($K_{p2}$, defined below) should be as large as possible for the same combination to effectively separate the rhodium from the heavies. In calculating the partition coefficient for rhodium ($K_{p2}$), the concentration of rhodium in the polar and non-polar phases are measured by atomic absorption, inductively coupled plasma, and other techniques as known to those having ordinary skill in the art, but the same measurement techniques should be used to measure concentration in both phases. The partition coefficient for rhodium ($K_{p2}$) is defined as:

$$Kp2 = \frac{\text{Concentration of rhodium in polar phase}}{\text{Concentration of rhodium in nonpolar phase}}$$

When $K_{p2}$ is high, the rhodium is being retained in the polar phase and will be recycled back to the reaction zone rather than lost with the heavies removal stream (the non-polar phase). When the phases are of equal volume, $K_{p2}$ should be at least 2.5, preferably above 5, and most preferably above 10.

$K_{p2}$ can be estimated by the partition coffined of the monophosphite ligand as the rhodium-ligand complex exhibits similar solubility behavior to the ligand itself. The concentration of the monophosphite ligand is in general much easier to measure than the concentration of rhodium. The partition coefficient for monophosphites according to formula (I) ($K_{p2'}$) is defined as:

$$Kp2' = \frac{\text{Concentration of ligand in polar phase}}{\text{Concentration of ligand in nonpolar phase}}$$

When $K_{p2'}$ is high, the rhodium is being retained in the polar phase and will be recycled back to the reaction zone rather than lost with the heavies removal stream (the non-polar phase). When the phases are of equal volume, $K_{p2}$ should be at least 2.5, preferably above 5, and most preferably above 10.

An efficiency factor (Ef) can also be calculated by dividing the partition coefficient of rhodium ($K_{p2}$) by the partition coefficient of the heavies ($K_{p1}$) as shown:

$$Ef = \frac{Kp2}{Kp1}$$

In some embodiments of the present invention, the polar and nonpolar solvent are selected so as to maximize the efficiency factor as this would indicate that most of the heavies have separated into the nonpolar phase and most of the ligand/rhodium has separated into the polar phase. In some embodiments, the polar and nonpolar solvents are selected so as to provide and efficiency factor (Ef) of 25 or higher. In some embodiments, the polar and nonpolar solvents are selected so as to provide and efficiency factor (Ef) of 30 or higher. In some embodiments, the polar and nonpolar solvents are selected so as to provide and efficiency factor (Ef) of 100 or higher.

Figure 2:
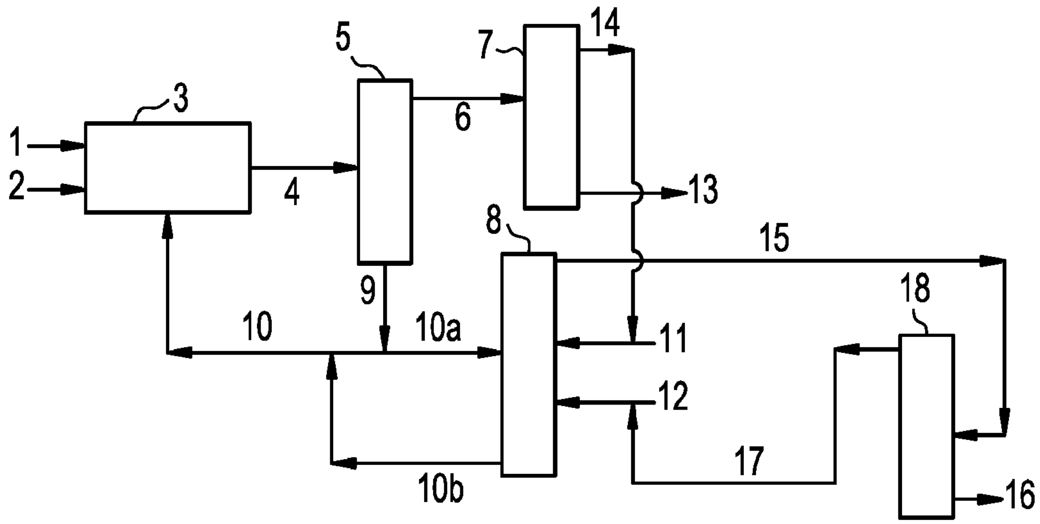
FIG. 2 is a schematic of a system for implementing some embodiments of processes of the present invention.
Figure 3:
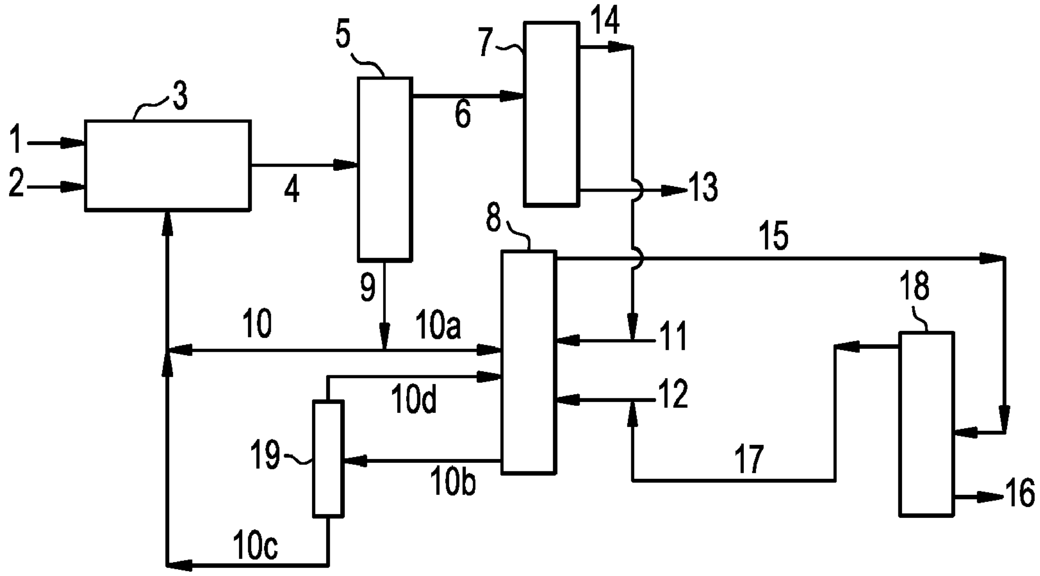
FIG. 3 is a schematic of a system for implementing some embodiments of processes of the present invention.

FIGS. 2 and 3 are schematics of systems for implementing some embodiments of processes of the present invention.

In FIG. 2, syngas (1) and olefin (2) are added to one or more hydroformylation reaction zones (3). A portion of the hydroformylation reaction product fluid is withdrawn via line (4) to one or more product/catalyst separation zones (e.g., vaporizer) (5) wherein an overhead stream (6) comprising the bulk of the aldehyde product is removed and a non-volatiziled stream (9) comprising the catalyst and heavies is recovered. A portion of stream (9) is sent back to the reaction zone (3) via line (10) and a portion is sent via line (10*a*) to the liquid-liquid separation zone (8). Polar solvent (fresh from line (11) or optionally with recycled solvent via line (14)) and non-polar solvent (fresh from line (12) or optionally with recycled solvent via line (17)) are added and a phase separation occurs. The top (non-polar) layer comprising heavies (15) is removed and a bottoms stream (10*b*) is recovered and returned to the reaction zones (3) or product/catalyst separation zone (5). Stream (15) is optionally sent to a distillation system (18) to recover and recycle the non-polar solvent and desired aldehyde product. Likewise, stream (6) can be sent to an optional distillation system (7) to recover polar solvent and unreacted olefin and recycle back via line (14). Both stills (7) and (18) may recover both polar and non-polar solvents as well as some desired aldehyde depending on the compositions of the feed streams and the distillation conditions but all will be recovered and recycled in unit (8). The desired aldehyde product is removed via line (13) (if unit (7) is used) or simply via line (6) for further processing. The undesired heavies are removed via line (16) (if unit (18) is used) or simply via line (15). Since there is minimal catalyst present in stream (15), the distillation in (18) can be more harsh to effectively recover as much solvent and desired aldehyde product without concerns about catalyst loss. Stream (14) may be distilled prior to recycling to unit (8) but typically is used as produced since this stream may contain unreacted olefin thus effects some olefin recycle. A purge (not shown) may be present on (14) to address hydrocarbon or other inerts buildup if needed as well as syngas and inert gas purges.

FIG. 3 shows a system similar to the system of FIG. 2 wherein a portion, preferably the majority, of the bottom stream from the liquid-liquid separation zone (8) is sent to a distillation system (19) to recover the polar solvent and optionally any remaining non-polar solvent (via line 10*d*) before sending the catalyst stream back to the reaction zone or product/catalyst separation zone via line (10*c*). This optional process can reduce the concentration of inerts in the reaction zone and is useful when the polar solvent may contribute to side reactions (e.g., water or alcohols).

Additionally, some solvent combinations may form azeotropes which will enhance the vaporization and distillation processes. For example, small amounts of water in the product/catalyst separation zone (e.g., vaporizer) (5) or distillation stills (7), (18) and/or (19) can azeotrope acetonitrile and cyclohexane which will enhance their recovery and recycle.

Illustrative non-optically active aldehyde products that can be produced using hydroformylation processes of the present invention include e.g., 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methyladipaldehyde, 3-methyladipaldehyde, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Some embodiments of the present invention will now be described in more detail in the following Examples.

EXAMPLES

All parts and percentages in the following examples are by weight unless otherwise indicated. Pressures are given as absolute pressure unless otherwise indicated.

General Procedure for Continuous Hydroformylation Process

The hydroformylation process is conducted in a glass pressure reactor operating in a continuous mode. The reactor consists of a three ounce pressure bottle partially submersed in an oil bath with a glass front for viewing. After purging the system with nitrogen, about 20-30 mL of a freshly prepared rhodium catalyst precursor solution is charged to the reactor with a syringe. The catalyst precursor solution contains about 50 ppmw rhodium (introduced as rhodium dicarbonyl acetylacetonate), the specified ligand, and tetraglyme as solvent. After sealing the reactor, the system is purged with nitrogen and the oil bath is heated to furnish the desired hydroformylation reaction temperature. The hydroformylation reaction is conducted at a total pressure of 150 to 160 psig (1034 to 1103 kPa) and at a temperature of ~70° C. A feed comprising nitrogen, syngas, and propylene is started. The flows of the feed gases ($H_2$, CO, propylene, $N_2$) are controlled individually with mass flow meters and the combined feed gases are dispersed in the catalyst precursor solution via fritted sparger. The partial pressures of $N_2$, $H_2$, CO, propylene, and aldehyde products are determined by analyzing the vent stream by GC analysis and Dalton's Law. The unreacted portion of the feed gases is continuously vented allowing for stripping out butyraldehydes products and maintaining substantially constant liquid level. Flows and feed gas partial pressures are set to obtain hydroformylation reaction rates up to 4 gram-moles aldehyde per liter reaction fluid per hour. The outlet gas is analyzed continuously by GC. Samples of the reaction fluid are withdrawn (via syringe) for rhodium analysis by Atomic Absorption, and/or HPLC analyses to confirm catalyst composition and feed purity. In practice, it is often observed that the system takes about one day to arrive at steady state conditions due to removing trace air from feed lines and reaching thermal equilibration of oil baths. This equipment also allows for generating hydroformylation rates as a function of reaction temperature, CO and $H_2$ partial pressures, and Rh content. Reaction rates are converted to a constant olefin partial pressure to allow comparisons (first order olefin kinetics are assumed).

General Procedure for Batch Hydroformylation Process

In an autoclave Parr reactor, 30 mL of 1-octene is added. The reactor is blanketed with a 1:1 mixture of CO/$H_2$ by pressurizing/depressurizing the reactor from 200 psi to 50 psi five times at room temperature. The reactor is then allowed to stir at 70° C. under 200 psi of a mixture of CO/$H_2$ atmosphere (1:1).

A solution of the ligand to be tested (1 mL, 10 eq., 112 μmol) is added followed by a solution of rhodium dicarbonyl acetylacetonate (1 mL, 1 eq., 11.2 μmol) in acetonitrile solvent. The control ligand was delivered as a toluene solution and the inventive ligand delivered in acetonitrile.

The reaction is followed by continuously monitoring the volume of the CO/$H_2$ (1:1) mixture being fed to the reactor to maintain the reactor pressure using a Brooks totalizer.

Example 1: Ligand A Synthesis

Ligand A (as shown above) is an example of a compound of the present invention according to formula (I) and can be synthesized as follows. To a stirring solution of 2,3-dimethoxyphenol (10 g, 65 mmol) and tert-butanol (7.44 mL, 78 mmol, 1.2 eq.) in toluene (10 mL) at 90° C. is added sulfuric acid (0.2 mL, 4 mmol, 0.05 eq.) dropwise under inert atmosphere. After stirring overnight, the solution is cooled, diluted in water and extracted with diethylether (3*50 mL). The combined organic extracts are washed with brine and dried over sodium sulfate. After filtration, the solvent is removed under vacuum to yield 95% yield (12.954 g, 62 mmol) of 2-(tert-butyl)-4,5-dimethoxyphenol which is used without further purification. The structure of the Ligand A precursor is confirmed by 1H NMR analysis and 13C NMR analysis:

$^1$H NMR (400 MHZ, Chloroform-d) δ 6.83 (s, 1H), 6.60 (d, 1H), 6.32 (s, 1H), 4.95 (s, 1H), 3.83 (s, 3H), 3.77 (s, 3H), 1.39 (s, 9H). 13C NMR (101 MHz, $CDCl_3$) δ 148.25, 147.61, 142.18, 127.47, 112.25, 102.22, 57.03, 55.91, 34.13, 29.84.

To a stirring solution of 2-(tert-butyl)-4,5-dimethoxyphenol (1 g, 4.75 mmol) and triethylamine (0.729 mL, 5.23 mmol, 1.1 eq.) in dichloromethane (10 mL) is added phosphorus trichloride (0.124 mL, 1.43 mmol, 0.3 eq.) is added dropwise at room temperature. The solution is stirred overnight, filtered and the solvent removed under vacuum to yield the product tris(4,5-dimethoxy-2-tbutylphenyl)phosphite at 98% yield (0.921 g, 4.5 mmol) which is used without further purification. The structure of Ligand A is confirmed by 1H NMR analysis, $^{13}$C NMR analysis, and $^{31}$P NMR analysis:

$^1$H NMR (400 MHZ, Chloroform-d) § 6.94 (d, 1H), 6.89 (s, 1H), 3.85 (s, 3H), 3.66 (s, 3H), 1.36 (s, 9H). $^{13}$C NMR (101 MHz, $CDCl_3$) δ 147.16, 144.68, 144.27, 131.70, 111.58, 105.02, 56.53, 55.78, 34.49, 30.24. $^{31}$P NMR (162 MHZ, CDCl3) δ 130.33.

Example 2 and Control Example 1

Hydroformylation experiments are performed (continuous reactor mode) in order to compare the reaction rate of tris-(2-tertbutyl-4-(propxy-2-one)phenyl)phosphite (Ligand A) against a control ligand, tris-(2,4-ditertbutylphenyl)phosphite (Control), a well known prior art ligand. Ligand A and the Control were run at equal Ligand/Rh ratios.

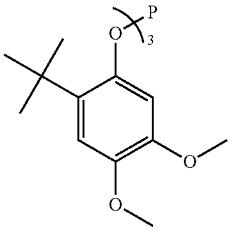

tris(4,5-dimethoxy-2-tertbutylphenyl)phosphite
(Ligand A)

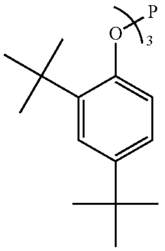

tris(2,4-diterbutylphenyl)phosphite
(Control)

The testing conditions are as follows:

TABLE 4

| Continuous Testing Conditions | | | | | |
|---|---|---|---|---|---|
| Olefin propylene Rh (ppmw) | Solvent tetraglyme Temp (° C.) | Ligand Ligand A or Control CO (psi) | Ligand A/Rh 10.0 $H_2$ (psi) | Target rate (g-mol/1-hr) 1 Olefin (psi) | Olefin Propylene Total flow (sL/hr) |
| 50 | 70 | 50 | 50 | 5 | 30 |

The reaction are continuously monitored by GC to give a reaction rate and the product selectivity from the normal versus iso-aldehyde (i.e., N/I ratio). The results are presented in Table 5:

TABLE 5

| Testing Results | | | | |
|---|---|---|---|---|
| Elapsed time | tris-(2,4-ditertbutylphenyl) phosphite (Control) | | Ligand A | |
| (Days/Hrs/M/S) | Rate | N/I | Rate | N/I |
| 0:0:00:00 | 0.0033 | 0.39 | 0.0918 | 0.75 |
| 0:11:55:04 | 0.7236 | 1.17 | 0.5494 | 1.10 |
| 0:23:55:04 | 0.5764 | 1.21 | 0.4999 | 1.11 |
| 1:11:50:08 | 0.4002 | 1.19 | 0.4364 | 1.09 |
| 2:0:40:09 | 0.4289 | 1.22 | 0.4751 | 1.12 |
| 2:12:35:14 | 0.3463 | 1.18 | 0.4317 | 1.11 |
| 3:0:30:15 | 0.3391 | 1.19 | 0.4322 | 1.11 |
| 3:12:30:18 | 0.3239 | 1.20 | 0.4203 | 1.10 |
| 4:0:25:22 | 0.3253 | 1.19 | 0.4207 | 1.10 |
| 4:12:20:24 | 0.2998 | 1.19 | 0.4087 | 1.09 |
| 5:0:15:26 | 0.3083 | 1.21 | 0.4222 | 1.11 |
| 5:12:10:27 | 0.2985 | 1.19 | 0.4002 | 1.10 |
| 6:0:05:31 | 0.2788 | 1.22 | 0.4106 | 1.09 |
| 6:12:05:32 | 0.2778 | 1.18 | 0.3894 | 1.09 |
| 7:0:00:36 | 0.3062 | 1.21 | 0.4047 | 1.10 |
| 7:11:55:38 | 0.2645 | 1.19 | 0.3946 | 1.09 |
| 8:0:45:41 | 0.2767 | 1.19 | 0.4310 | 1.10 |
| 8:12:40:44 | 0.2750 | 1.19 | 0.4654 | 1.11 |
| 8:20:55:43 | 0.2611 | 1.21 | 0.4325 | 1.11 |

The data in Table 5 shows that Ligand A and the Control display similar activities at steady state conditions as well as a similar N/I ratio of 1.1-1.2. The above data confirm that monophosphite ligands (compounds according to formula (I)) of the present invention are effective ligands for the preparation of effective and stable hydroformylation catalysts.

Example 3: General Procedure for Ligand Partitioning ($K_{p2'}$) Experiments

The partitioning of the monophosphite ligands according to some embodiments of the present invention (compounds according to formula (I)) in a mixture of biphasic acetonitrile (polar) and hexane (nonpolar) are then studied as follows: In a nitrogen-filled glove box, a mixture of acetonitrile (5 mL), hexane (5 mL) and 100 mg of the ligand to be tested are mixed for 30 minutes. The stirring is stopped and the two phases are left to phase separate for another 30 minutes. Using a 1 mL syringe, 0.2 mL of the top phase (the hexane phase (nonpolar)) and the bottom phase (the acetonitrile phase (polar)) are sampled and diluted to 1 mL with a 1 wt % solution of cyclohexyldiphenyl phosphine (CHDPP, an oxygen scavenger) in tetraglyme. The samples are analyzed by HPLC analysis with a method for which they have been previously calibrated to determine the ligand content in each phase, and the partition coefficient ($K_{p2'}$) is calculated using the formula above. The results obtained are shown in Table 6:

TABLE 6

| Sample | Solvent System | Phase | Area Count | Partition Coefficient |
|---|---|---|---|---|
| Ligand A | Hexane/Acetonitrile | Top | 142046 | |
| (Example 3) | | Bottom | 1458674 | 9.98 |
| Control | Hexane/Acetonitrile | Top | 2426123 | |
| (CE 2) | | Bottom | 96727 | 0.04 |

The data shows how Ligand A partitions favorably in the polar phase compared to the prior art ligand.

Examples 4-8 and Comparative Examples 3-8: Determination of Ef for Optimal Heavies Removal with Minimal Catalyst Loss A series of partition experiments similar to Example 3 are done with a number of aldehydes and models for aldehyde heavies. Texanol (isobutyraldehyde trimer) is used to model $C_4$ heavies and isopropylpalmitate was used to model a $C_8$ trimer. 2-Ethyl-hexenal and octanal were used to model low polarity $C_3$ dimer and $C_4$ dimer, respectively. Nonanal models a non-polar, mixed $C_4/C_5$ dimer (e.g., en-al after mixed aldol condensation or mixed ether byproduct). A sample of a monophosphite catalyst solution used for branched octene hydroformylation is concentrated under vacuum to remove the bulk of the Co aldehyde product then this sample comprising Co trimers ("INA Trimers") is tested. The concentration in each phase is determined by GC (the Co trimers were a large number of peaks which are summed together). As shown in Table 7, when Kpi is no greater than 1.0, the phase separation process will give optimal heavies removal with minimal rhodium losses as shown by Ef values greater than 25 and several well above 100 using the Ligand A partition coefficient from Table 6 above ($K_{p2}$=9.98 for Ligand A). Heavies such as $C_4$ trimer with ester and alcohol moieties that are polar (e.g., Texanol) will not partition appropriately (Ef<10) but less polar, higher molecular weight heavies such as $C_8$ or $C_9$ heaves will be effectively removed via this process. In Table 7, "a" represents the top (nonpolar) layer and "b" represents the bottom (polar) layer.

TABLE 7

| Estimation of liquid-liquid extraction for heavies removal. | | | | | | | | |
|---|---|---|---|---|---|---|---|---|
| | | | Average Area counts | Dilution factor | Concentration | $K_{p1}$ | $K_{p2'}$ | Ef |
| Ex 4 | nonanal | 3a | 4804054 | 7.44 | 35745926 | 0.22 | 9.98 | 46 |
| | | 3b | 1232396 | 6.33 | 7798753 | | | |
| Ex 5 | isopropyl palmitate | 4a | 6153899 | 7.14 | 43929516 | 0.10 | 9.98 | 100 |
| | (C19 ester) | 4b | 639082 | 6.87 | 4388930 | | | |

TABLE 7-continued

Estimation of liquid-liquid extraction for heavies removal.

| | | | Average Area counts | Dilution factor | Concentration | $K_{p1}$ | $K_{p2'}$ | Ef |
|---|---|---|---|---|---|---|---|---|
| Ex 6 | INA Trimers | 5a | 82430397 | 2.33 | 192062825 | 0.013 | 9.98 | 764 |
| | | 5b | 1076761 | 2.33 | 2508853 | | | |
| CE3 | Texanol (C4 Trimer) | CE3a | 1246875 | 7.61 | 9488641 | 2.90 | 9.98 | 3 |
| | | CE3b | 4188851 | 6.57 | 27530819 | | | |
| CE4 | 2-methylpentanal | CE4a | 2895904 | 7.90 | 22874765 | 1.25 | 9.98 | 8 |
| | | CE4b | 4348398 | 6.58 | 28622095 | | | |
| CE5 | Octanal | CE5a | 3685319 | 8.55 | 31514458 | 1.10 | 9.98 | 9 |
| | | CE5b | 5442152 | 6.35 | 34533486 | | | |
| CE6 | 2-Ethyl-hexenal (C4 dimer) | CE6a | 2731006 | 7.11 | 19410111 | 2.00 | 9.98 | 5 |
| | | CE6b | 6224311 | 6.25 | 38897606 | | | |

a = top,
b = bottom layer

To test the performance of monophosphite ligands according to formula (I) for higher olefins, 1-octene is used as the olefin in a batch reactor. The heavies generated by this system would be the same as the isononyl alcohol trimers tested in Example 6 above (thus the relevant $K_{p1}$ given in Table 7 above will be used to calculate Ef values below). The results are shown in Table 8:

TABLE 8

Batch hydroformylation results of 1-Octene with Ligand A compared to Control

| | Conversion (%) | Selectivity (N/I) | Rate (mole/L*Hr) |
|---|---|---|---|
| CE 7 | 97.62 | 1.49 | 0.096 |
| Example 7: Ligand A | 96.79 | 1.69 | 0.104 |

Ligand A conversion, selectivity, and rate are comparable to the Control ligand. The important next step is to demonstrate that catalysts using Ligand A can be effectively removed from the catalyst mixture with removal of the heavies with minimal rhodium loss (Ef).

Example 8 and Comparative Example 8: The reactor samples from Comparative Example 7 and Example 7 are measured for rhodium content and then 1 g of each reactor crude mixture (1-Octene hydroformylation reaction product fluid with Control ligand or Ligand A) are mixed with 4 grams of acetonitrile and 4 grams of hexane. After allowing the phases to separate, the rhodium content of each phase is measured. The results are given below based on $K_{p1}$ taken from Table 7 for INA trimer (Ex. 3):

TABLE 9

Partition of C9 aldehyde heavies with rhodium retention (Ef determination)

| | | Rh Concentration (ppmw) | Partition coefficient (Hexane/ Acetonitrile) | Partition coefficient (Acetonitrile/ Hexane) $Kp_2$ | $Kp_1$ | Ef | Rh mass balance |
|---|---|---|---|---|---|---|---|
| CE8 | Crude | 54.6 | | | | | |
| | Hexane | 12.4 | 5.93 | 0.17 | 0.013 | 13 | 106 |
| | Acetonitrile | 2.09 | | | | | |
| Ligand A | Crude | 55.4 | | | | | |
| (Ex 7) | Hexane | 0.52 | 0.043 | 23.46 | 0.013 | 1796 | 97 |
| | Acetonitrile | 12.2 | | | | | |

Ligand A has clearly a superior Ef value relative to the Control ligand, and clearly the phase separation of the system will effectively recover the majority of the rhodium while very effectively removing the heavies from the catalyst solution. This result also confirms the correlation of $K_{p2}$ with $K_{p2}$ wherein the prediction based on the former is validated by the actual catalyst testing.

What is claimed is:

1. A transition metal complex hydroformylation catalytic precursor composition consisting essentially of a solubilized Group VIII transition metal-monophosphite complex, an organic solvent, and free monophosphite ligand, wherein the monophosphite ligand of the metal-monophosphite complex and the free monophosphite ligand are each a compound the following formula:

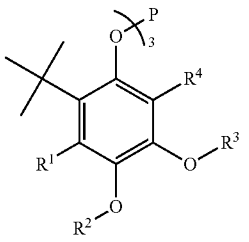

wherein $R^1$-$R^4$ are the same or different and each individually represent an hydrogen, a monovalent hydrocarbyl or substituted hydrocarbyl radical selected from alkyl, arylalkyl, and alicyclic radicals.

2. The transition metal complex hydroformylation catalytic precursor composition of claim 1, wherein the monophosphite ligand of the metal-monophosphite complex and the free monophosphite ligand are the same compound.

3. A process for separating one or more heavies from a hydroformylation reaction product fluid comprising a metal-monophosphite ligand complex catalyst, optionally free monophosphite ligand, one or more aldehyde products, and heavies, the process comprising:

(a) hydroformylating a $C_6$ to $C_{40}$ mono-olefin with the metal-monophosphite ligand complex catalyst and optionally free monophosphite ligand in a reaction zone to provide a hydroformylation reaction product fluid, wherein the monophosphite ligand of the metal-monophosphite ligand complex catalyst is a compound according to the following formula:

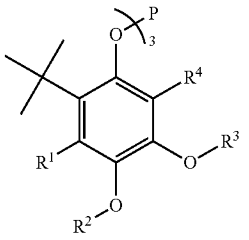

wherein $R^1$-$R^4$ are the same or different and each individually represent an hydrogen, a monovalent hydrocarbyl or substituted hydrocarbyl radical selected from alkyl, arylalkyl, and alicyclic radicals;

(b) removing a portion of the hydroformylation reaction product fluid from the reaction zone and transferring the portion to a product/catalyst separation zone wherein a portion of the aldehyde products are vaporized as an overhead stream and wherein a non-volatilized catalyst fluid comprising the metal-monophosphite ligand complex catalyst is recovered as a bottoms stream;

(c) mixing at least a portion of the bottoms stream obtained in step (b) in the presence of a nonpolar solvent and a polar solvent to obtain, by phase separation, two phases: a first phase comprising the polar solvent, the metal-monophosphite ligand complex catalyst and optionally free monophosphite ligand, and a second phase comprising the non-polar solvent, a portion of the heavies, and at least a portion of the remaining aldehyde products; and (d) recovering said metal-monophosphite ligand complex catalyst and at least a portion of any free monophosite ligand from the first phase and returning the recovered metal-monphosphite ligand complex catalyst and any recovered free monophosphite ligand to the reaction zone.

4. The process of claim 3, wherein the recovered metal-monophosphite ligand complex catalyst and any recovered free monophosphite ligand from step (d) can be used in the reaction zone without further treatment.

5. The process of claim 3, wherein the polar solvent present in step (d) is removed from the first phase prior to the recovered metal-monophosphite ligand complex catalyst and any recovered free monophosphite ligand being returned to the reaction zone.

6. The process according to claim 3, wherein the non-polar solvent is distilled from the second phase in step (d) and at least partially recycled.

7. The process according to claim 3, wherein the non-polar solvent comprises a $C_6$-$C_{40}$ mono-olefin and is the same as the mono-olefin being hydroformylated in step (a).

8. The process according to claim 3, wherein the non-polar solvent comprises unreacted mono-olefin that is recovered from the overhead stream in step (b).

9. The process according to claim 3, wherein the second phase comprising non-polar solvent and heavies isolated in step (c) is further processed to recover residual aldehyde product.

10. The process according to claim 3, wherein at least a portion of the nonpolar solvent and/or polar solvent used in step (c) is provided with the bottoms stream from step (b).

11. A hydroformylation process for producing aldehydes, the process comprising:

reacting an olefinically unsaturated compound selected from the group consisting of alpha-olefins containing from 6 to 40 carbon atoms, internal olefins containing from 6 to 40 carbon atoms, and mixtures of such alpha and internal olefins with carbon monoxide and hydrogen in a reaction zone in the presence of a rhodium-monophosphite complex catalyst consisting essentially of rhodium complexed with carbon monoxide and at least one monophosphite ligand, wherein the at least one monophosphite ligand is a compound according to the following formula:

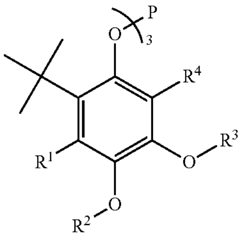

wherein $R^1$-$R^4$ are the same or different and each individually represent an hydrogen, a monovalent hydrocarbyl or substituted hydrocarbyl radical selected from alkyl, arylalkyl, and alicyclic radicals.

12. The process according to claim 11, wherein the reaction zone further comprises at least one free monophosphite ligand, wherein the at least one free monophosphite ligand is a compound according to the following formula:

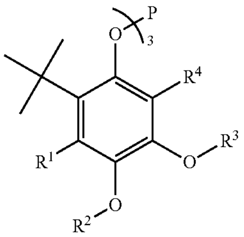

wherein $R^1$-$R^4$ are the same or different and each individually represent an hydrogen, a monovalent hydrocarbyl or substituted hydrocarbyl radical selected from alkyl, arylalkyl, and alicyclic radicals.

13. The process of claim 11, wherein the hydroformylation reaction conditions comprise: a reaction temperature from 50° C. to 120° C., a total gas pressure of hydrogen, carbon monoxide, and olefinically unsaturated organic compound from 1 to 1500 psia, a hydrogen partial pressure from 15 to 200 psia, and a carbon monoxide partial pressure from 10 to 200 psia, and wherein the reaction zone contains from 4 to 200 moles of said monophosphite ligand per mole of rhodium.

14. The process according to claim 11, wherein the concentration of rhodium in the reaction zone is 5 to 500 ppmw.

* * * * *